(12) United States Patent
Phallen et al.

(10) Patent No.: US 6,189,736 B1
(45) Date of Patent: Feb. 20, 2001

(54) CONDIMENT DISPENSING APPARATUS

(75) Inventors: Iver J. Phallen, Youngstown; Douglas N. Vogt, Pavilion, both of NY (US)

(73) Assignee: Niagara Pump Corporation, Buffalo, NY (US)

( * ) Notice: Under 35 U.S.C. 154(b), the term of this patent shall be extended for 0 days.

(21) Appl. No.: 09/380,652

(22) PCT Filed: Mar. 11, 1998

(86) PCT No.: PCT/US98/04754

§ 371 Date: Sep. 7, 1999

§ 102(e) Date: Sep. 7, 1999

(87) PCT Pub. No.: WO98/40309

PCT Pub. Date: Sep. 17, 1998

Related U.S. Application Data

(63) Continuation-in-part of application No. 09/341,443, filed as application No. PCT/US98/00958 on Jan. 16, 1998.
(60) Provisional application No. 60/036,115, filed on Jan. 17, 1997, and provisional application No. 60/040,232, filed on Mar. 11, 1997.

(51) Int. Cl.[7] ........................................................ B67D 5/08
(52) U.S. Cl. .............................. 222/52; 222/63; 222/105; 222/144.5; 222/207; 222/214
(58) Field of Search .................................... 222/52, 63, 95, 222/105, 144.5, 207, 214, 571, 639

(56) References Cited

U.S. PATENT DOCUMENTS

| | | |
|---|---|---|
| 1,922,196 | 8/1933 | Butler . |
| 2,105,200 | 1/1938 | Phelps . |
| 2,393,838 | 1/1946 | Tarbox . |
| 2,412,397 | 12/1946 | Harper . |
| 2,926,614 | 3/1960 | Rose . |
| 2,971,471 | 2/1961 | Huebschman . |
| 3,046,903 | 7/1962 | Jones . |
| 3,048,121 | 8/1962 | Sheesley . |
| 3,154,021 | 10/1964 | Vick . |
| 3,158,104 | 11/1964 | Hutchinson . |
| 3,263,617 | 8/1966 | Johnson . |
| 3,318,251 | 5/1967 | Smith . |
| 3,349,716 | 10/1967 | Weber . |
| 3,518,033 | 6/1970 | Anderson . |
| 3,724,973 | 4/1973 | Shill . |
| 3,724,974 | 4/1973 | Molimard . |
| 3,811,800 | 5/1974 | Shill . |
| 3,822,720 | 7/1974 | Souza . |
| 3,829,249 | 8/1974 | Pursley . |

(List continued on next page.)

FOREIGN PATENT DOCUMENTS

| | | |
|---|---|---|
| 74594/74 | 10/1974 | (AU) . |
| 32368/89 | 10/1989 | (AU) . |
| 1426963 | 3/1976 | (GB) . |
| 2020735 | 11/1979 | (GB) . |
| 2057067 | 3/1981 | (GB) . |
| 2257478 | 1/1993 | (GB) . |
| WO 92/16450 A1 | 10/1992 | (WO) . |
| WO 94/21918 A1 | 9/1994 | (WO) . |

Primary Examiner—Kevin Shaver
Assistant Examiner—David Deal
(74) Attorney, Agent, or Firm—John C. Thompson

(57) ABSTRACT

A condiment dispensing apparatus for dispensing condiments from a bag-in-box type container (108). There is a high durometer compressible elastomeric liquid flow tube (14), an infeed and outfeed thereto and therefrom, and a movable anvil (26) with a round surface to compress the tube. There is an opposed stationary anvil (28) which holds the tube for compression by the movable anvil. The tube is held between the anvils (26, 28) in a slightly compressed state even when the anvil is retracted. There is a control assembly (FIG. 15) that causes extension and retraction of the movable anvil to cause flow through the tube, and subsequent delivery of condiment to a dispensing fixture (110).

49 Claims, 32 Drawing Sheets

U.S. PATENT DOCUMENTS

| | | |
|---|---|---|
| 3,902,490 | 9/1975 | Jacobsen et al. . |
| 3,983,857 | 10/1976 | O'Connor . |
| 3,998,103 | 12/1976 | Björklund et al. . |
| 4,014,318 | 3/1977 | Dockum et al. . |
| 4,360,324 | 11/1982 | Ohara et al. . |
| 4,410,322 | 10/1983 | Archibald . |
| 4,413,751 | 11/1983 | Tokorozawa . |
| 4,477,003 | 10/1984 | Baker et al. . |
| 4,479,797 | 10/1984 | Kobayashi et al. . |
| 4,500,266 | 2/1985 | Cummins . |
| 4,501,405 | 2/1985 | Usry . |
| 4,558,989 | 12/1985 | Chappell . |
| 4,657,490 | 4/1987 | Abbott . |
| 4,722,372 | 2/1988 | Hoffman et al. . |
| 4,789,016 | 12/1988 | Mihail . |
| 4,886,432 | 12/1989 | Kimberlin . |
| 4,893,991 | 1/1990 | Heminway et al. . |
| 4,967,940 | 11/1990 | Blette et al. . |
| 5,011,378 | 4/1991 | Brown et al. . |
| 5,049,047 | 9/1991 | Polaschegg et al. . |
| 5,082,429 | 1/1992 | Soderquist et al. . |
| 5,088,522 | 2/1992 | Rath et al. . |
| 5,113,753 | 5/1992 | Robinson . |
| 5,113,754 | 5/1992 | Robinson et al. . |
| 5,131,816 | 7/1992 | Brown et al. . |
| 5,151,019 | 9/1992 | Danby et al. . |
| 5,158,210 | 10/1992 | Du . |
| 5,165,873 | 11/1992 | Meijer . |
| 5,199,852 | 4/1993 | Danby . |
| 5,209,654 | 5/1993 | Nilsson et al. . |
| 5,217,355 | 6/1993 | Hyman et al. . |
| 5,222,980 | 6/1993 | Gealow . |
| 5,230,443 | 7/1993 | Du . |
| 5,242,083 | 9/1993 | Christine et al. . |
| 5,242,279 | 9/1993 | Knuth . |
| 5,252,044 | 10/1993 | Raines et al. . |
| 5,273,406 | 12/1993 | Feygin . |
| 5,290,158 | 3/1994 | Okada . |
| 5,302,093 | 4/1994 | Owens et al. . |
| 5,316,452 | 5/1994 | Bogen et al. . |
| 5,320,503 | 6/1994 | Davis . |
| 5,342,180 | 8/1994 | Daoud . |
| 5,349,825 | 9/1994 | Duke et al. . |
| 5,352,103 | 10/1994 | Auer . |
| 5,361,943 | 11/1994 | Du . |
| 5,361,944 | 11/1994 | Hauf et al. . |
| 5,364,242 | 11/1994 | Olsen . |
| 5,366,117 | 11/1994 | Mesenbring et al. . |
| 5,368,195 | 11/1994 | Pleet et al. . |
| 5,370,510 | 12/1994 | Sinclair . |
| 5,380,172 | 1/1995 | Ulbing . |
| 5,401,139 | 3/1995 | Nabity et al. . |
| 5,405,252 | 4/1995 | Nikkanen . |
| 5,554,013 | 9/1996 | Owens et al. . |
| 5,556,258 | 9/1996 | Lange et al. . |
| 5,577,891 | 11/1996 | Loughnane et al. . |
| 5,584,667 | 12/1996 | Davis . |
| 5,588,816 | 12/1996 | Abbott et al. . |
| 5,593,290 | 1/1997 | Greisch et al. . |
| 5,624,056 | 4/1997 | Martindale . |
| 5,906,296 | 5/1999 | Martindale et al. . |

CONDIMENT DISPENSING APPARATUS

CROSS REFERENCE TO RELATED APPLICATIONS

This application is a continuation-in-part of U.S. application Ser. No. 09/341,443, filed Jul. 9, 1999, which is in turn a 371 of PCT/US98/00958, filed Jan. 16, 1998, said PCT application claiming priority from U.S. provisional application 60/036,115 filed Jan. 17, 1997 and U.S. provisional application 60/040,232 filed Mar. 11, 1997.

TECHNICAL FIELD

The present invention relates generally to a condiment dispensing apparatus, and more particularly to an electronically controlled liquid condiment dispensing apparatus utilizing a novel linear peristaltic pump as the liquid pumping elements.

BACKGROUND OF THE INVENTION

Liquid condiments such as catsup (ketchup), mustard, mayonnaise, sauces of all types, salad dressings, syrups, gravies, oils, dairy products coffee creamers and sweeteners, food toppings, flavoring and juices are widely utilized in restaurants of all types. It is a frequent practice to make condiments freely available to restaurant customers for application to the fare of the restaurant, as the customer may desire. This practice is generally known as self serve. Means to do this presently include prepackaged portions contained in small pre-made bags known generally as packets, a manually operated pumping apparatus integrated into a stainless steel holding pot, and serving pots containing spoons or scoops, and squeeze bottles.

Each of the described means of providing self serve condiments to a restaurant patron offers limitations. In the case of the packets, they are very expensive and their use is uncontrolled and wasteful. For example, one study showed that 30% or more of all packets taken by restaurant customers were either discarded as refuse or removed from the restaurant. In the case of squeeze bottles or pots using scoops or pumps, a great deal of the condiment placed into these reservoirs is not recoverable. In addition, these means of presenting condiments frequently suffer from severe problems of clogging, sanitation, contamination and are often aesthetically unappealing in appearance, particularly as condiments congeal or dry and cake on the edges and walls of such reservoirs. It is also important to note that these same condiment dispensing methods, problems and limitations are found in restaurant kitchens as well. Because of these and other problems which will be detailed further on, improved means of providing condiment dispensing in restaurants of every sort is necessary.

OBJECTS AND SUMMARY OF THE INVENTION

It is a primary object of the present invention to overcome the numerous limitations and disadvantages of known liquid condiment dispensing methods as set forth above. Furthermore, the objects of this invention include providing:

1. Automatic condiment dispensers using either one of two disclosed unique types of linear peristaltic pumps as the means of condiment displacement.
2. Automatic condiment dispenser systems particularly suited to dispensing all types of liquid food products and condiments.
3. Automatic condiments dispensers particularly suited to cleaning and sanitizing in place without the necessity of disassembly or replacement.
4. An automatic condiment dispensing system in which all control and system integration functions are electronically derived.
5. An automatic condiment dispensing system which includes the ability to electronically select a dose or on demand (metered) flow.
6. An automatic condiment dispensing system which includes the ability to select for the use of an electronically operated point of dispense positive shut-off valve to achieve a no drip cut-off of the condiment, after dispensing.
7. The ability to use reverse pumped flow to achieve a no drip-cut-off of condiment, after dispensing.
8. The ability to electronically determine the condiment dose volume where a dose mode of operation has been selected.
9. The ability to electronically dispense, on a priority input basis, to more than one location using a single pump, such that only one location at a time is served.
10. The ability to electronically signal dispenser status and diagnostics to a local annunciator panel or to a Programmable Logic Controller or computer and thus to a wide area computer network.
11. The ability to electronically signal and thus record and document condiment usage for purpose of inventory keeping and automatic ordering and re-supply.
12. An automatic condiment dispense system capable of effectively dispensing ketchup, mustard or mayonnaise at a distance of 100 feet from the condiment displacement pump.
13. An automatic condiment dispenser system which utilizes pumps which are particularly designed so as not to compress gas pockets found in condiment products to such a degree as to cause explosive decompression of these gas pockets when they exit to atmosphere at the point of dispense.
14. A design for a condiment dispenser system primarily intended for placement under a counter or cabinet in a restaurant dining or public area.
15. A design for condiment dispenser system primarily intended for use in a restaurant kitchen or food preparation area.

DETAILED DESCRIPTION IN GENERAL

Figure 1:
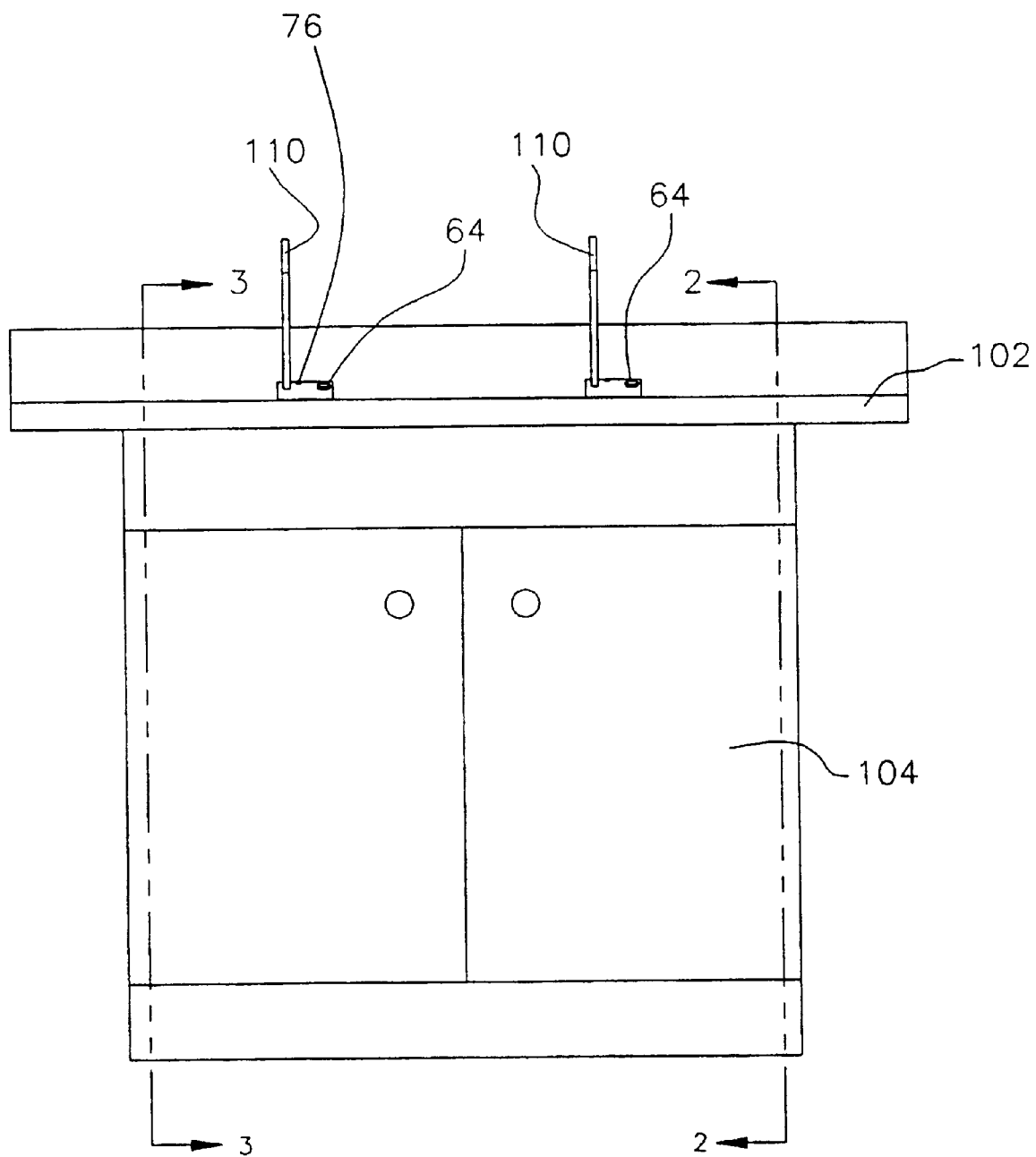
FIG. 1 illustrates a typical under counter installation of two electronically controlled liquid condiment dispensers having presentation fixtures mounted on the top of a counter, the condiment dispenser being mounted within the cabinet.

The present invention consists of electronically controlled condiment dispensers. Two preferred embodiments are disclosed, one generally intended for self serve use in the public areas of restaurants, and one for the kitchen or food preparation area of the restaurant.

Two different pumps are suitable for use with the described dispenser systems. One is described fully in co-pending application PCT/US98/00958, and is briefly described below. The second pump type is unique and novel and is fully described in this patent specification.

The condiment dispensers described herein consist of stands particularly designed to hold a bulk supply of condiment, the positive displacement dispensing pump, the particular means of mounting the pump to the stand, the flexible rubbing required to connect the pump to the supply, the flexible tubing needed to connect the outfeed of the pump to the point of dispense, and the point of dispense apparatus.

CHECK VALVE—COMPRESSIVE CENTER SECTION—CHECK VALVE PUMP

The first novel and unique feature of the present invention consists of the check valve—compressive center section—check valve pump, the pumping means being indicated generally at 10.

This pump consists of a suitable infeed check valve assembly 12 connected to one end of a short section of high durometer flexible tubing 14, with an outfeed check valve assembly 16 connected to the other end. The check valves, which allow fluid in only on direction, are fitted such that both allow flow in the same direction. Disposed between the two check valves is a pneumatically operated displacement assembly 18. Each of the valves 12 and 16 are essentially identical and a cross section of valve 12 is shown in FIG. 13A. As can be seen from an inspection of this cross section, the valve consists of a valve body 12.1, infeed and outfeed barbs 12.2 and 12.3 which are screwed into the valve body 12.1. A cartridge 12.4 is disposed within the valve body 12.1. The valve body is provided with a seat 12.11 and when the parts are assembled, a ball 12.5 will be caused to bear against the seat 12.11 by a pressure spring 12.6. This spring is so selective that its cracking pressure will be 0.33 psi. In addition to the foregoing components, an annular seal 12.7 of the illustrated cross section is provided, the seal being positioned adjacent the seat 12.11 and in contact with the ball (when in its closed position) and the cartridge 12.4. O-ring seals 12.8 and 12.9 are also provided. The various components are made of suitable materials for use in a sanitary environment.

Pumps using two check valves connected by an intervening flexible element are well known in the art. Sheesley (U.S. Pat. No. 3,048,121) describes a "flexible diaphragm pump" which is hydraulically operated with an infeed check valve and outfeed check valve, the pump requiring positive liquid feed pressure in order to operate. Hutchinson (U.S. Pat. No. 3,158,104) describes a dual check valve pump wherein the flexible center section is hydraulically compressed using a closely mounted plunger or piston pump as a hydraulic pump. Weber (U.S. Pat. No. 3,349,716) teaches a flexible displacement tube which is situated on a flat backer plate and is acted upon by an arc shaped plunger which is driven by a rotary motion actuated connecting rod. Shill (U.S. Pat. No. 3,724,973) teaches a dual check valve blood pump where the flexible center displacement element is compressed circumferentially by gas pressure and wherein the rebound of the tube is assisted by vacuum, and whereby the compression and rebound times are fluidically adjustable. Dockum (U.S. Pat. No. 4,014,318) discloses an implantable blood pump wherein the flexible tube is compressed by an electric solenoid directly coupled to an arc shaped compressive member. Bogen (U.S. Pat. No. 5,316,452) teaches a compressible displacement tube actuated by an "electrically driven reciprocating hammer actuator".

Figure 12:
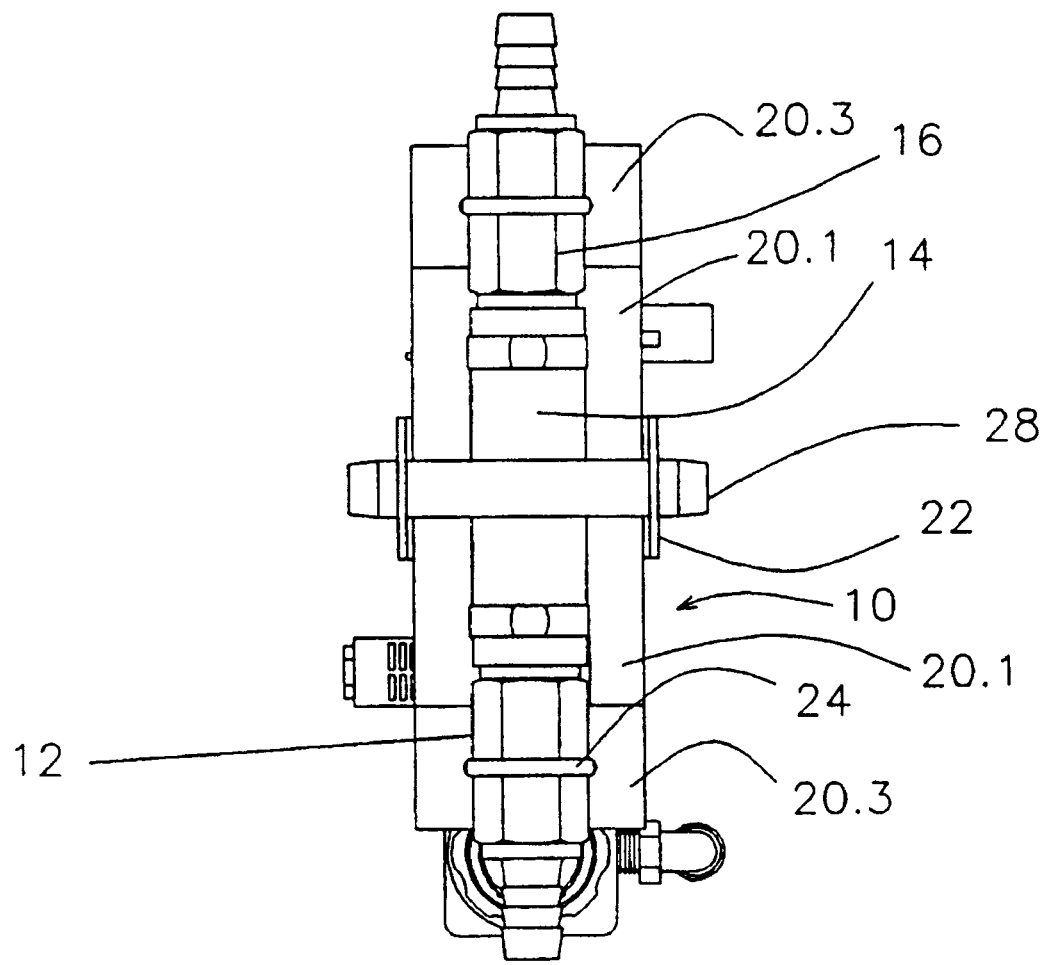
FIG. 12 is an enlarged back view of the check valve—compressive center section—check valve pump shown, for example, in FIG. 10.
Figure 13:
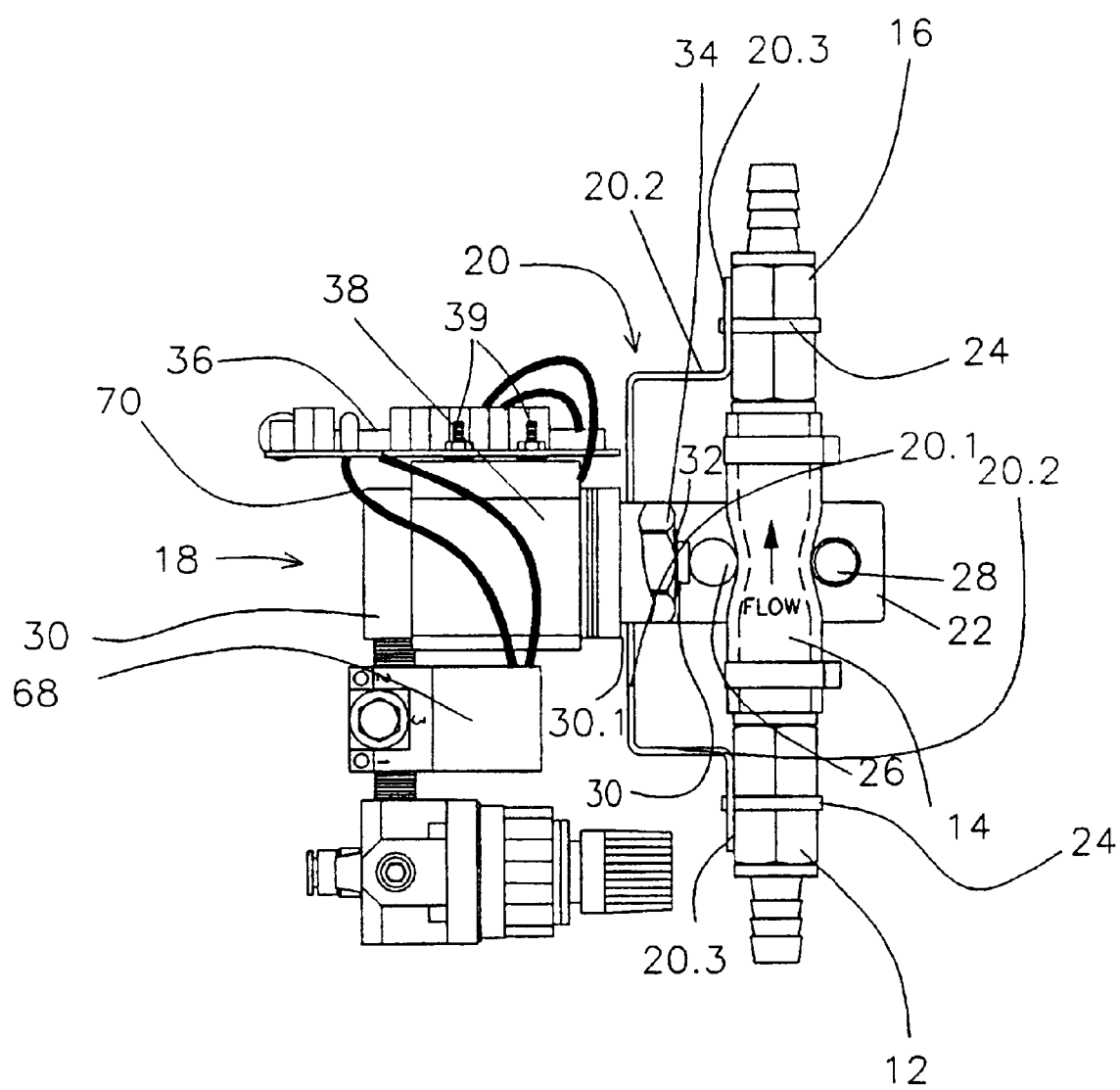
FIG. 13 is a right side view of the pump shown in FIG. 11.
Figure 13A:
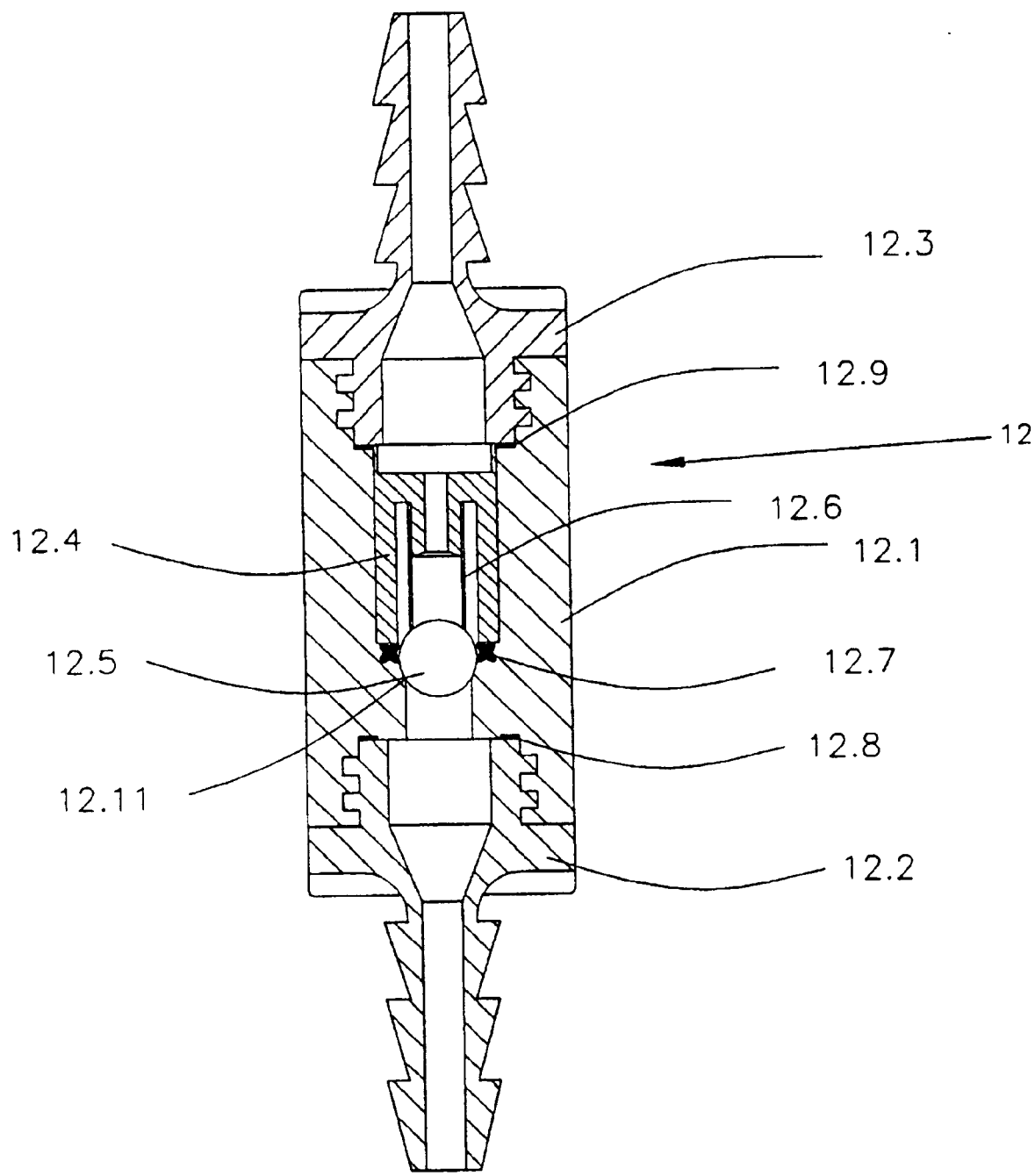
FIG. 13A is a cutaway view of one of the check valve units utilized in the pump shown in FIGS. 12 and 13.
Figure 14A:
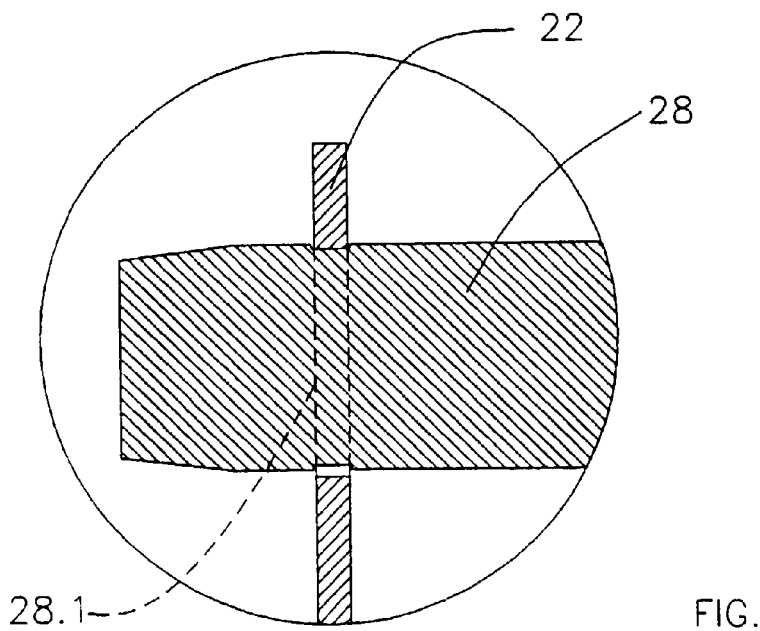
FIG. 14A is an enlargement of a portion of FIG. 14.
Figure 14:
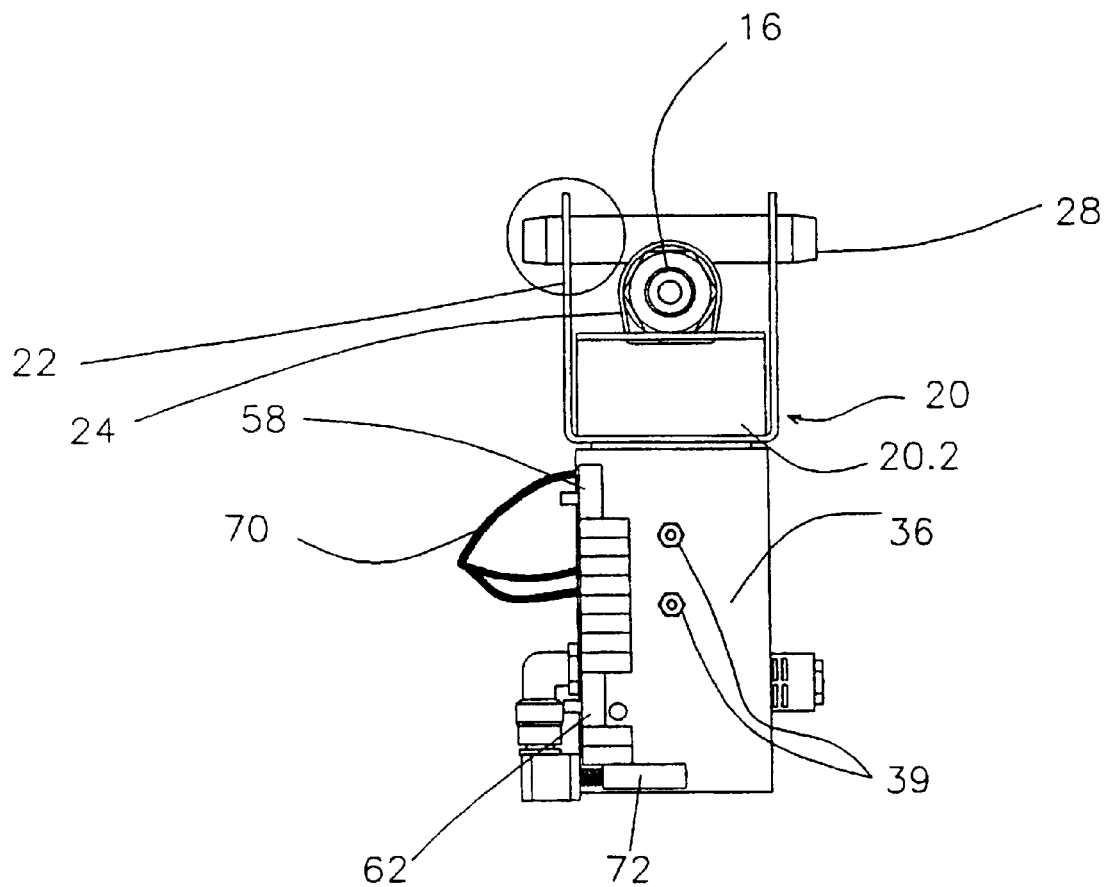
FIG. 14 is a top view of the pump shown in FIGS. 12 and 13.
Figure 15:
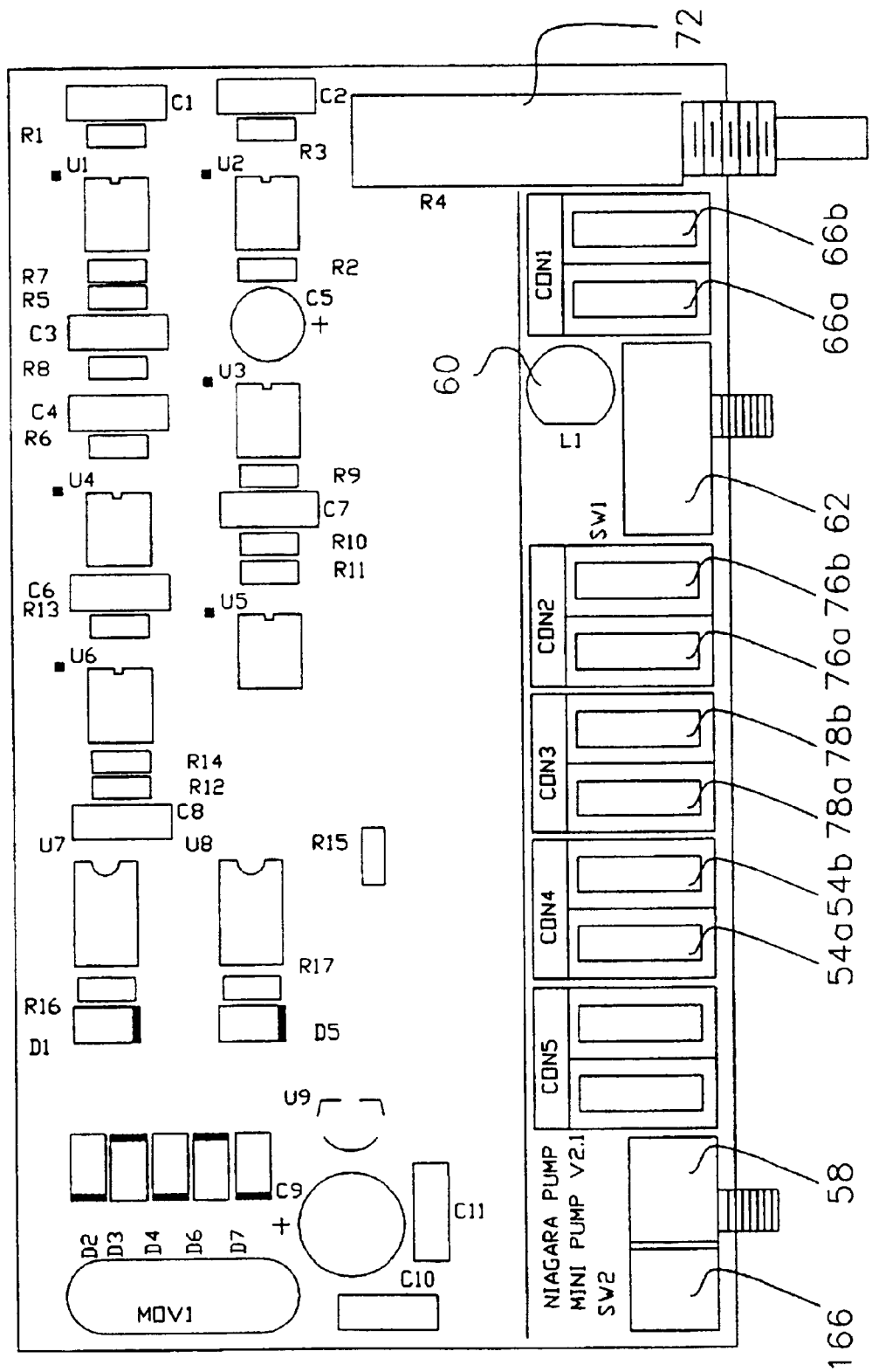
FIG. 15 is a view of the electronic controller used with the pump shown in FIGS. 12 and 13.

In the present invention, as can best be seen from FIGS. 12–14, the pump frame to support the dual check valve-flexible hose fluid pathway and the compression element used to cyclically compress the pump hose is constructed using stainless steel sheet. The frame uniquely consists of only two parts, a check valve mount plate 20 and an upper anvil mount plate 22. The valve mount plate consists of a flat intermediate section 20.1 generally spanning the length of the flow tube. At each end of the flat section 20.1, the plate turns at 90 degrees and an extension section 20.2 extends toward each check valve. After an interval, the plate 20 again turns 90 degrees away from the center line of the pump. The result of this shape is to create a platform 20.3 at each end of the valve mount plate upon which the check valves rest and to which they are affixed. The extension sections 20.2 also provides means for uniquely mounting the pump within the condiment dispenser as will be detailed further on. The check valves can be fastened to their respective platforms by many means, but in the preferred embodiment a simple plastic cable tie 24 is used. Two holes 20.4 are provided on each valve platform suitably spaced to allow the cable tie to pass around the valve and through the platform. Thus fastened, the pump tube is assured of being centered on compression anvils 26, 28 at right angles to the flow axis of the pump, compression anvil 26 being carried by a piston rod 29 by means of a spring pin (as shown in PCT/US98/00958), which piston rod is connected to a piston within a pneumatically operated cylinder assembly 30. The other anvil 28 is carried by the mounting plate 22. This method offers durability, simplicity and the ties are easily removed and replacement easily re-installed upon the infrequent changing out of the fluid flow pathway of the pump. The vertical elevation o the valve mount plate is sufficient in any given size of the pump to generally center the outer walls of the pump tube 14 between the two opposing compression anvils in the pump displacement section. As best shown in FIG. 14, the upper anvil mount 22 is a U-shaped piece having a bight portion 22.1 which spans across the flat bottom section of the valve mount plate at 90 degrees to the long axis of the pump and is located at the center line of the anvil-actuator assembly. The upper anvil mount is located against the bottom surface of the valve mount plate such that it is captured between the shoulder 30.1 of the actuating pneumatic cylinder assembly 30 and the valve mount plate. The result of this arrangement is the creation of a very stiff and strong anvil mount. The two frame pieces are assembled together using the threaded nose piece 32 and nut 34 of the actuation air cylinder. This single fastener uniquely serves to assemble the entire pump frame and actuator assembly.

The spaced apart sides 22.2 of the U-shaped upper anvil mount and each provided with hole, (no number) on each side, suitably spaced to allow insertion of the compressions anvil 28 which is in the shape of a round rod, typically made of stainless steel. The anvil 28, when inserted, serves to capture and pre-compress the pump flow tube 14. The upper anvil 28 is provided with two circumferential grooves 28.1, one disposed toward each end of the anvil. When installed into the pump, these grooves engage with the mount anvil holes in the sides 22.2 of the upper anvil mount as shown in FIG. 14A, thus securely capturing the upper anvil. The overall geometry and function of the compression anvils 26, 28 and the pneumatic actuator assembly 18 are analogous to that described for the displacement section of the three-element pump described in co-pending application PCT/US98/00958, and will thus not be discussed herein.

The pump of the present invention is novel in that the pneumatically operated cylinder displacement assembly 18 is provided to act directly upon the flexible and compressive pump tube in order to effect compression of the tube and hence liquid displacement. Pumps of the prior art disclose circumferential gas and hydraulic enclosures surrounding the pump tube, motor coupled linkage driven compression assemblies, and solenoid driven compressive elements, but fail to disclose direct compression of a dual check valve pump using a pneumatic cylinder assembly.

Another unique feature of the pump of the present invention is the ability, by virtue of the method of construction, to directly visually inspect all aspects of the unit for correctness of fluid flow pathway positioning, anvil positioning and overall assembly.

Still another novel feature of the pump of the present invention is that pump mechanism contains only five mechanical moving parts or elements in order to produce pumping. These are the solenoid valve, the pneumatic cylinder-anvil assembly, the pump tube, the infeed check valve, and the outfeed check valve. This economy of moving parts contributes to great simplicity of construction and exceptional reliability.

The check valve—compressive center section—check valve pump of the present invention incorporates many of the novel features with the pump described in co-pending application PCT application Ser. No. PCT/US98/00958. While these will not be reviewed herein, for the sake of clarity, these common features will be briefly described as referenced by the listing of novel features described in the co-pending specification:

1. First Novel Feature: Method of construction
2. Second Novel Feature: Symmetrical dual round tube compression anvil design.
3. Third Novel Feature: Force multiplication.
4. Fourth Novel Feature: Use of a thick-walled, multi-layer, laminated, compound reinforced, high durometer, high pressure rated liquid pump tube.
5. Sixth Novel Feature: Positioning of the ends of the pump tube fittings within a multiple of 1.20 to 2.00 displacement actuator anvils.
6. Ninth Novel Feature: Direct close coupling of the electrically operated pneumatic solenoid valve to the pneumatic port of the air cylinder displacement actuator.
7. Eleventh Novel Feature: The use of an encoded actuator.
8. Twelfth Novel Feature: High viscosity priming capability.
9. Thirteenth Novel Feature: Methods of liquid flow rate control, of which the first, second, fifth and sixth methods are applicable.

The means of pumping of the dual check valve pump 10 of the present invention is straight forward. The pneumatic air cylinder actuator 18, the pressure of which is regulated by a pneumatic regulator 35 acting upon the flexible pump tube 14, serves to compress the tube, to variable degree as determined by the control electronics, thus causing the infeed check valve 12 to be reverse flow pressurized, and causing the outfeed check valve 16 to be forced open. When the pneumatic cylinder is depressurized, the stiff walled pump tube 12 forces it to reverse direction and the pump tube rebounds to a more open or uncompressed condition. This opening creates a lumen or volume greater than that at compression, thus causing the infeed check valve to be opened to flow due to the differential pressure created between the lumen (low) and the liquid in the infeed tubing (high) as acted upon by atmospheric pressure. (The terms "low" and "high" are relative to each other).

When the pump of the present invention is in a dry condition and is to be primed with liquid, the pumping action previously described must displace the gas in the pump to create a vacuum condition in order to draw liquid into the pump. In reference to this priming the pump of the present condition has two novel features.

As will be explained elsewhere in this specification, this dual check valve pump is particularly designed to be incapable of pumping gas at a significant discharge pressure. This is the case because the compressive stroke of the actuator reduces the volume of the pump tube lumen only partially and thus compresses the gas in the lumen only moderately. Because this is true, and because the pump must create sufficient vacuum over many cycles to suction prime viscous liquid materials such as ketchup, mustard and mayonnaise, the pump of the pressure of 0.33 pounds per square inch (⅓ PSI). This crucial check valve cracking pressure can be empirically demonstrated as being necessary for efficient and effective priming of the pump of the present invention.

Another unique feature of the pump of the present invention concerns the electronic control of priming. In some embodiments, it is beneficial to be able to vary the degree of pump tube compression and hence the displaced volume of the pump per cycle. When so configured, this capability allows easy adjustment of the flow rate of the pump as desired. However, a partial compression further reduces the gas pressure which can be generated in a dry suction priming situation, and may cause the outfeed check valve to fail to open at all. When this occurs, priming does not occur. To overcome this problem, the pump electronics can be uniquely designed such that a prime mode can be entered into, either by manual switch setting or by automatic change where after a certain number of uninterrupted pump cycles, the stroke of the displacement cylinder actuator is altered to become a full compressive or occlusive stroke and thus able to create the maximum possible gas displacement in order to maximize pump suction priming performance.

It is important to note that when equipped with the check valves described in this specification the check valve pump is not well suited to the pumping of liquids which contain solids of any significant size. Thus, this pump is largely intended for use in a condiment dispenser pumping smooth or unparticulated liquids such as catsup, smooth mustard, mayonnaise, oils and the like. Where particulated liquids are to be dispensed, the three element pump described in co-pending application PCT/US98/00958 is utilized, which pump is briefly described below. It should also be noted that the dual check valve pump detailed in this specification is capable of embodiments across a large scale of size and detail and is suitable for use in many diverse pumping applications and is thus not to be considered restricted in embodiments by this description.

Figure 16:
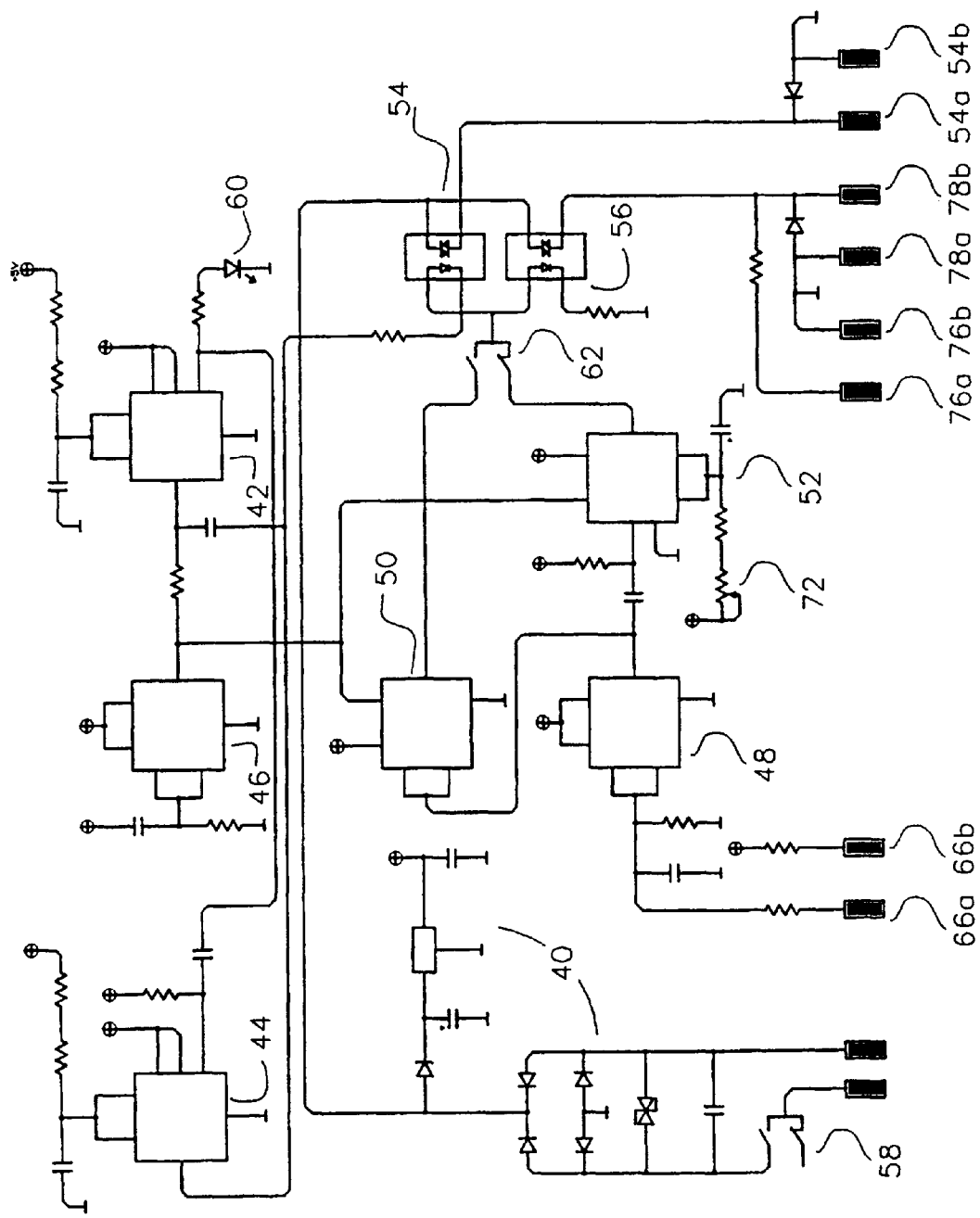
FIG. 16 is an electrical schematic of the circuit shown in FIG. 15.

The dual check valve pump herein described is designed to be controlled electronically. Thus, in its simplest embodiment, a control circuit card 36 is provided to be mounted directly onto the pump actuator by use of a suitable bracket or clip 38 which is secured to the card by suitable fasteners 39. In its simplest embodiment, the control card consists of an AC to DC power supply circuit 40 (FIG. 16), a timer circuit for actuator compression 42, a timer circuits for actuator retraction 44, a power-on initialization circuit 46, a run input buffer circuit 48, an on demand mode driver 50, an adjustable dose timer circuit 52, a pump valve driver 54 and a point of dispense (POD) valve driver 56. When used in a condiment dispenser, the inclusion of a selectable on demand and dose capability on the same electronic controller is unique.

In operation, a power switch 58 mounted on the circuit card 38 applies power to the circuit. Power is supplied to the pump electronic controller circuit card by use of a commercially available plug-in sealed plastic housed main AC transformer (not shown) which provides a 24 VAC output. This method assures a safe source of power at a low voltage, thus allowing the circuit card packaging to be limited to a moisture proof and corrosion resistant protective coating. The power-on initialization circuit assures that functions are properly initialized and also forces the pump actuator compression timer 42 to fire , which, in turn, forces the pump actuator retract timer 44 to fire. The retract timer then again fires the compression timer such that a self gated flip-flop or oscillator is established. Each timer period is separately established to achieve the desired pump function. An on card LED 60 is driven by the compression timer and provides a power on indicator and oscillator function indicator combined into the same device. Another circuit card mounted switch 62 allows selection between an on demand mode of operation and a timed dose mode of operation.

Figure 6:
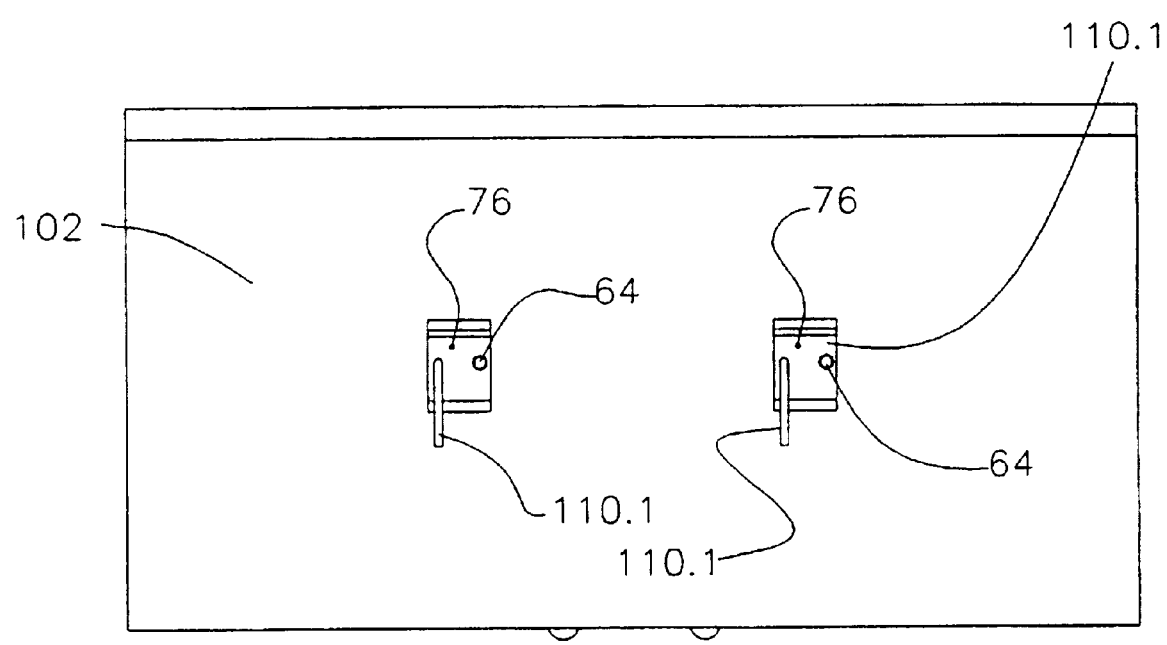
FIG. 6 is a top view of the dispenser assembly shown in FIG. 1.

In operation, a normally open momentary switch 64 (FIG. 6) connected to the run inputs 66a, 66b applies a signal to the input buffer 48. The buffer output allows the intermittent compression timer signal to be applied to the pump valve driver 54 which is connected to the pump solenoid control valve 68 (FIG. 13) through suitable leads 70 (FIG. 13) and terminals 54a, 54b, the signal in turn cyclically applying power to the pump valve solenoid coil. In the one demand mode, the pump cycle continues until the run switch 64 is opened. In the dose mode, the pump cycle continues until the pre-set dose time ends. The dose time is established using a board mounted potentiometer 72. The point of dispense valve driver 56 is continuously on whenever a run input is applied, and off when no run input is provided. This signal also is proved to separate connector positions 76a, 76b in order to allow the driving of an LED 76 (FIG. 6) located at the point of dispense, if desired. The point of dispense valve 78 is intended to allow a pneumatic solenoid operated valve to control a flow shut-off mechanism at the condiment point of dispense when such point is located a sufficient distance from the pump that clean cut-off of flow, free of drip or ooze, requires a local shut-off, the valve being connected to the card 36 via connectors 78a, 78b.

In conjunction with the use of the dose capability in combination with a positive shut-off device 79 (alternatively termed the flow shut-off mechanism); it is important to understand that the positive shut-off as shown in an electropneumatically actuated device, and that the does time uniquely controls the shut-off and that the shut-off cannot close off the flow or interrupt the dose before its completion. In dispensers known in the prior art (U.S. Pat. No. 5,366, 117), a dose mechanism is enabled in conjunction with a manually actuated liquid flow valve, but the liquid flow valve is not actuated or opened or maintained open by the dose mechanism. Thus, in a dose mode, if the manually opened valve is released before the dose is completed, the dose is interrupted and is partial in nature. The positive shut-off valve includes a pneumatically operated cylinder assembly similar to the pneumatic cylinder assembly 30. When operated to shut-off flow, an anvil bears upon a flexible tube to occlude the tube to effect shut-off. When air is released from the pneumatic air cylinder assembly of the shut-off valve the flexible tube will open. While the positive shut-off valve described is the preferred valve, it is possible to use other forms of shut-off valves.

Beyond the simplest embodiment of the pump control electronics above described, which is particularly suited for use in a simple and economical condiment dispensing system, many more capabilities are possible by use of control electronics substantially the same at that described as the Fourteenth Novel Feature of the co-pending Linear Peristaltic Pump application PCT/US98/00958. By omission of the infeed valve (IFV) and outfeed valve (OFV) control functions and capabilities dependent thereon, the novel capabilities and features embodied in the control electronics of the three element pump are directly applicable to the dual check valve pump particular to this application. These capabilities include the use of a microcontroller integrated circuit as the primary control engine, means of establishing metered flow, means of establishing dose volume, the provision for an electronic output firing signal, the use of pre-settable digital counters, the provision for multiple start inputs, the provision for a no liquid supply input signal to the pump with an associated pump inhibit and alarm output capability, the provision for automatic liquid supply changeover capability, and the provision for a run/count output signal.

Figure 18:
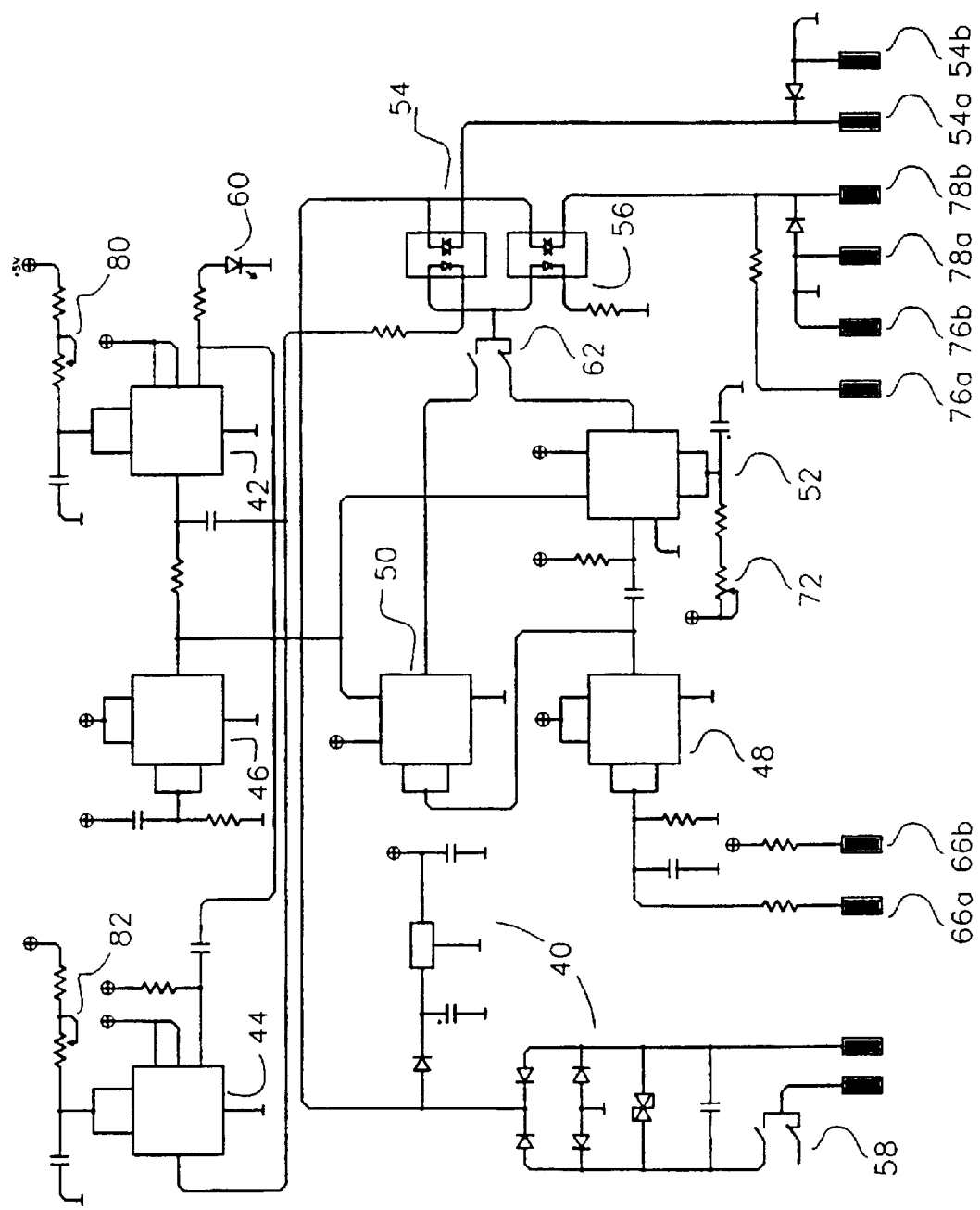
FIG. 18 is a view similar to FIG. 16 but illustrates the manner in which the compression time and retraction time of the compressive center section may be varied.

U.S. Pat. No. 3,724,974 discloses a dual check valve-flexible center element pump in which the compression time and the retraction times can be independently fluidically controlled. In the pump of the present invention, the compression time and the retraction time can be uniquely independently controlled and adjusted on an electronic basis via board mounted potentiometers 80, 82 as shown in FIG. 18. This novel capability provides important advantages. Adjustment of the compression time allows adjustment of the range of physical motion of the compression anvil, thus allowing direct electronic control of the displaced volume of the pump per pump cycle. This provides, in turn, direct electronic control of the flow rate of the pump. This can prove to be important and useful. For example, when used as the displacement pump in a condiment dispenser system as herein disclosed, it allows the flow rate of the pump to be modulated to produce a pleasing and gentle flow for delivery of condiments in a self serve setting while allowing much higher flow rates to be selected when the device is used to dispense condiments in a restaurant kitchen where faster speed of delivery is important to throughput.

In the case of independent electronic adjustment of the retraction time of the pneumatic piston displacement cylinder, more viscous liquids require a longer in-flow time into the pump in order to completely fill the pump lumen. Thus, the ability to increase the retraction time allows the pump to function free of cavitation across a broader range of liquid viscosities than would otherwise be the case. Further, electronically changing the retraction time can offer another means of flow rate adjustment where displacement per cycle is unaltered, but cycles per unit time is altered.

PUMP WITH THREE ACTUATING ASSEMBLIES WHICH AT UPON A PUMP TUBE

The pump with three actuating assemblies incorporates additional novel features of the pump described in co-pending application PCT/US98/00958. While these additional novel features will not be fully reviewed herein, for the sake of clarity, these additional common features will be briefly described as referenced by the listing of novel features described in the co-pending specification:

1. Fifth Novel Feature: Use of pressure rings in conjunction with pump tube.
2. Fourteenth Novel Feature: Electronic control capabilities.
3. Fifteenth Novel Feature: Ability of the pump to operate over a broad range of actuator pressure.
4. Sixteenth Novel Feature: Ability to pump highly particulated or non-homogeneous liquids and slurries.
5. Seventeenth Novel Feature: Inability of pump of displace gas at high pressure.

Figure 7:
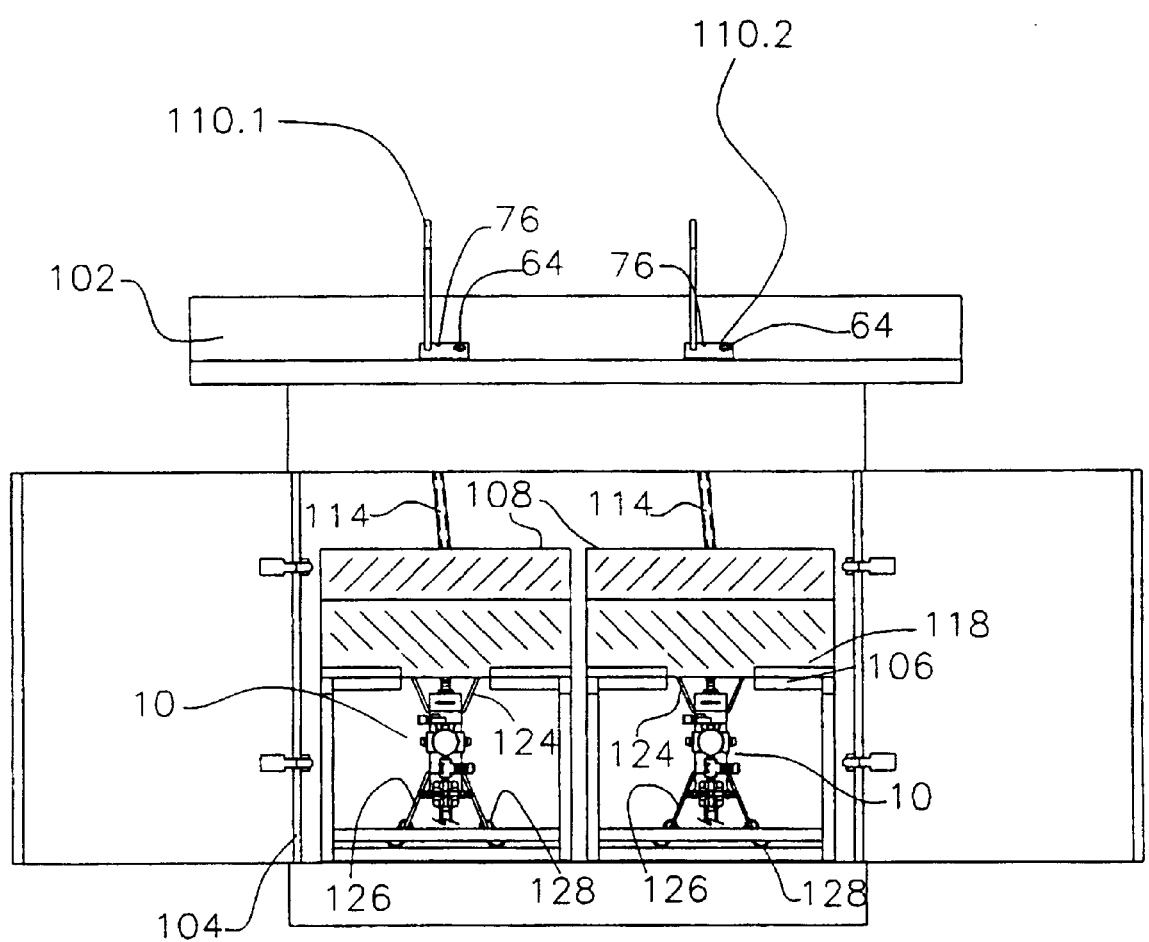
FIG. 7 is a view of FIG. 1 with the doors open.
Figure 8:
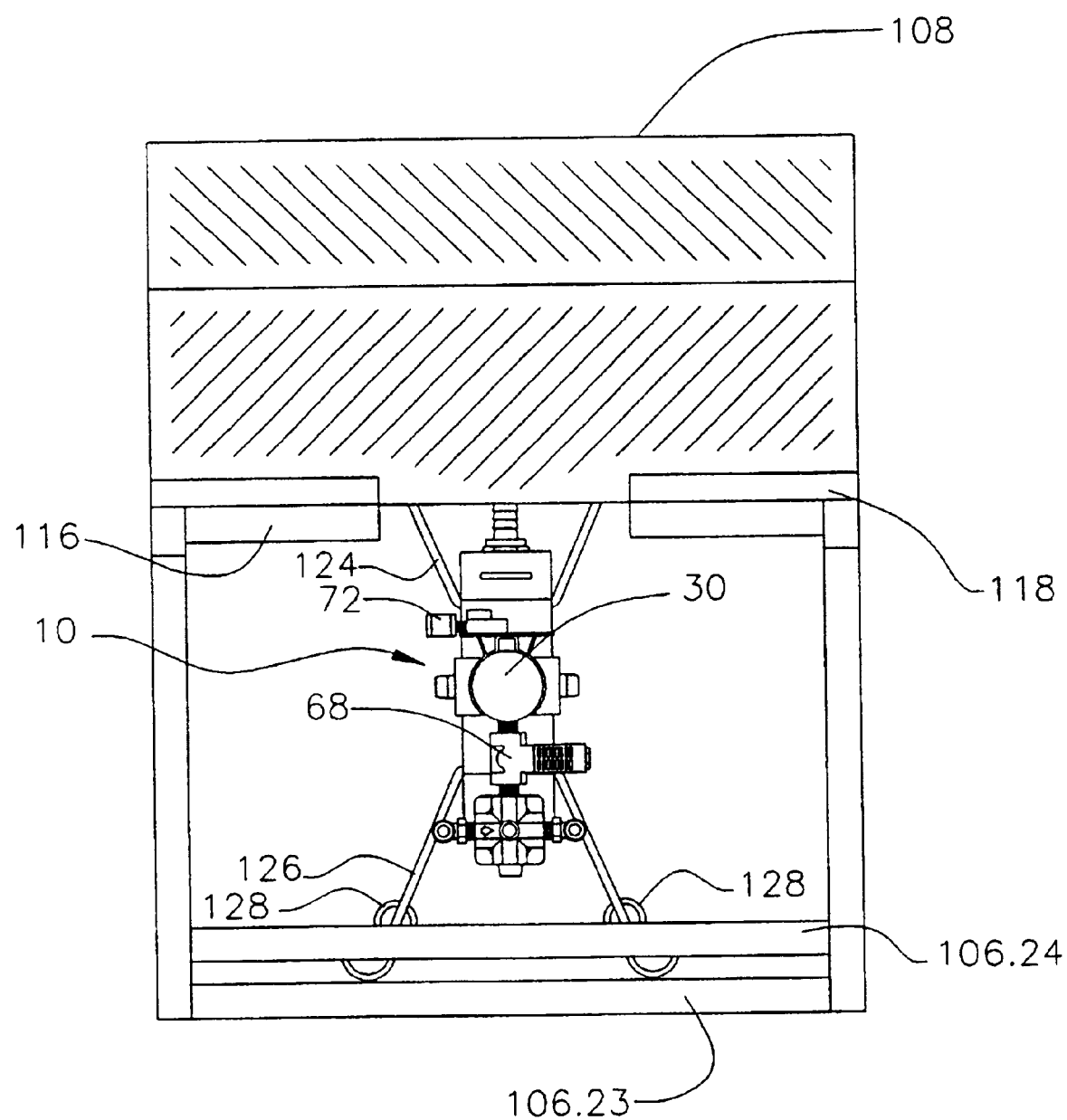
FIG. 8 is an enlarged view of a portion of FIG. 7.
Figure 8A:
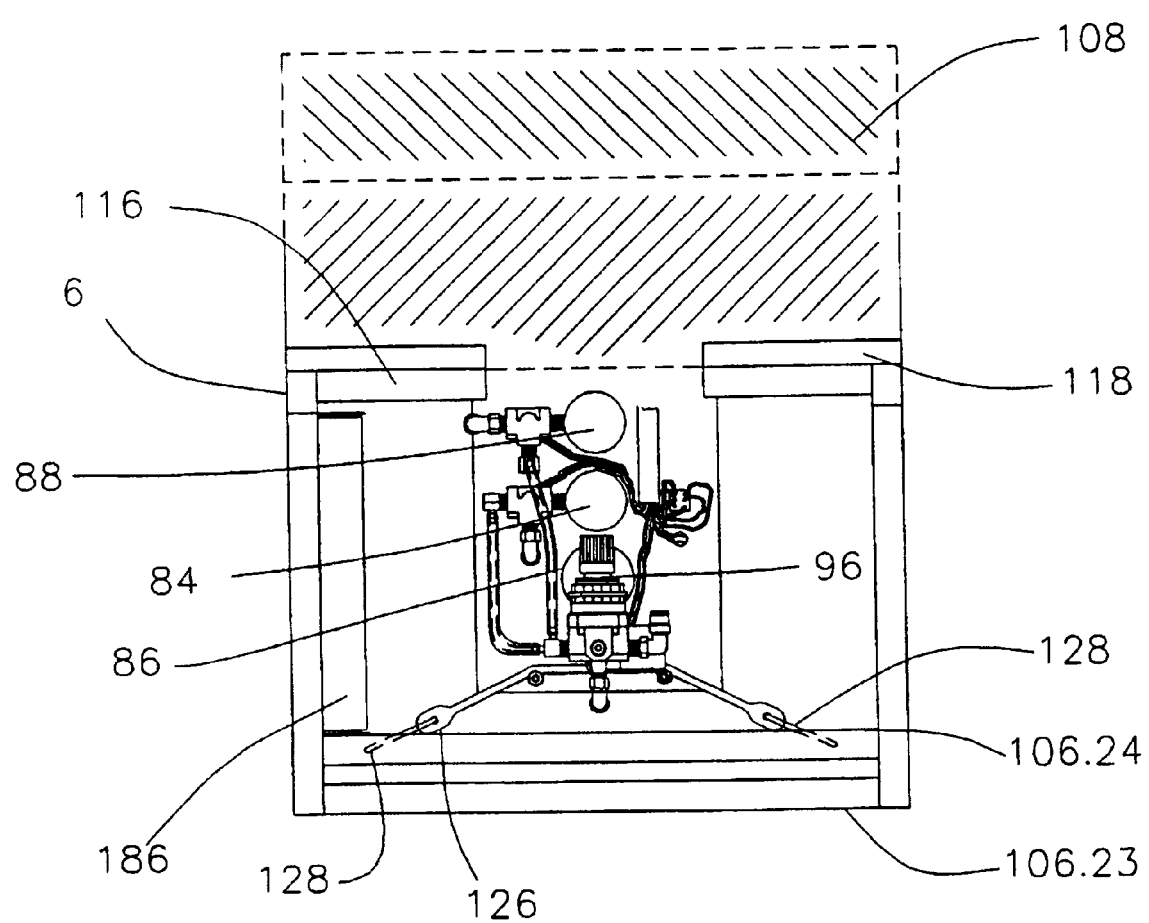
FIG. 8A is a view similar to FIG. 8 but showing a pump with three actuating assemblies.

In summary, the pump with three actuating assemblies is illustrated in FIGS. 4A, 5A, 8A, 9A, 10A, 11A, 20 and 21. Initially, it should be noted that while either the check valve—compressive center section—check valve pump assembly or the pump with three actuating assemblies may be used with the self serve condiment dispenser shown in FIGS. 7 and 17, the pump with three actuating assemblies is the preferred pump for the kitchen unit shown in FIGS. 20 and 21. It is also be preferred pump for condiments with particulates. As previously noted, the pump with three actuating assemblies is fully described in co-pending application Ser. No. PCT/US98/00958 filed on Jan. 16 1998. Therefore, reference should be made to that disclosure for a full description. However, the three actuating assembly pump, which is indicated generally at 83 in FIG. 4A. includes a central displacement actuator assembly 84 which is substantially identical to the displacement actuator assembly 18 of the check valve—compressive center section—check valve pump assembly described above. Instead of check valves it is provided with an infeed valve assembly which incorporates an actuator 86 and suitable anvils, and an outfeed valve assembly which incorporates an actuator 88 and other suitable anvils. Each of the actuators includes a piston rod which in turn carries an anvil which bears against a tube similar to tube 14. The tube is trapped between the anvils carried by the actuators and an anvil plate 90 which is held in place by pull pins 92 which pas through suitable apertures in a channel shaped support 94, which channel also receives the tube. The actuators are powered by air, the pressure of which is regulated by regulator 96. Operation of the actuators is controlled by solenoids 98 in response to an electronic controller 186 in a manner more fully set forth in the forgoing patent application. As can be seen from FIGS. 4A and 10A, an electronic controller 186 for each pump is supported by the metal frame 106. In the design shown in FIGS. 20–22, the electronic controller is located within a pump mount enclosure 180.

SELF SERVE CONDIMENT DISPENSER SYSTEM

Figure 2:
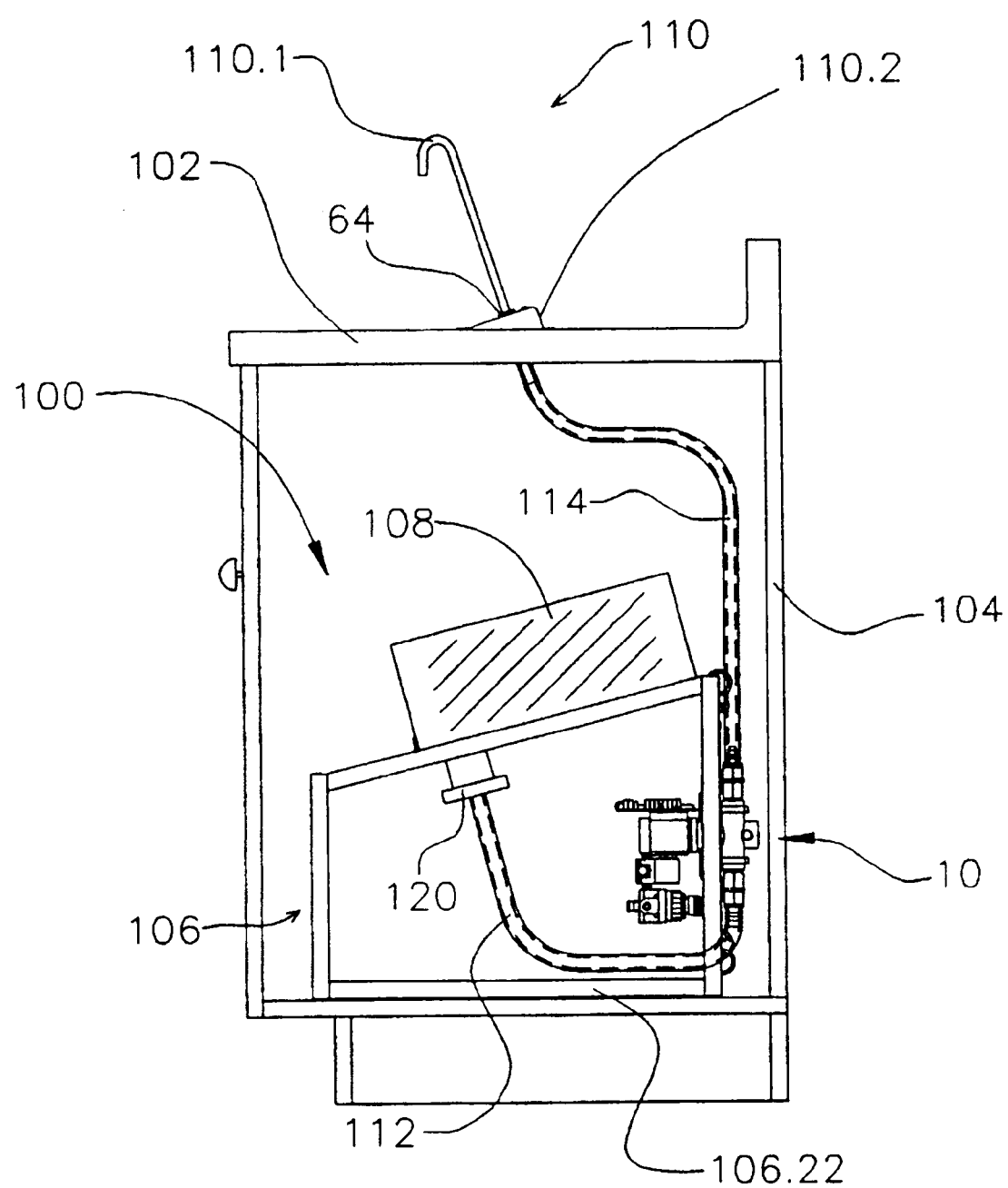
FIG. 2 is a right side view of the structure shown in FIG. 1, this view being taken generally along the line 2—2 in FIG. 1.
Figure 3:
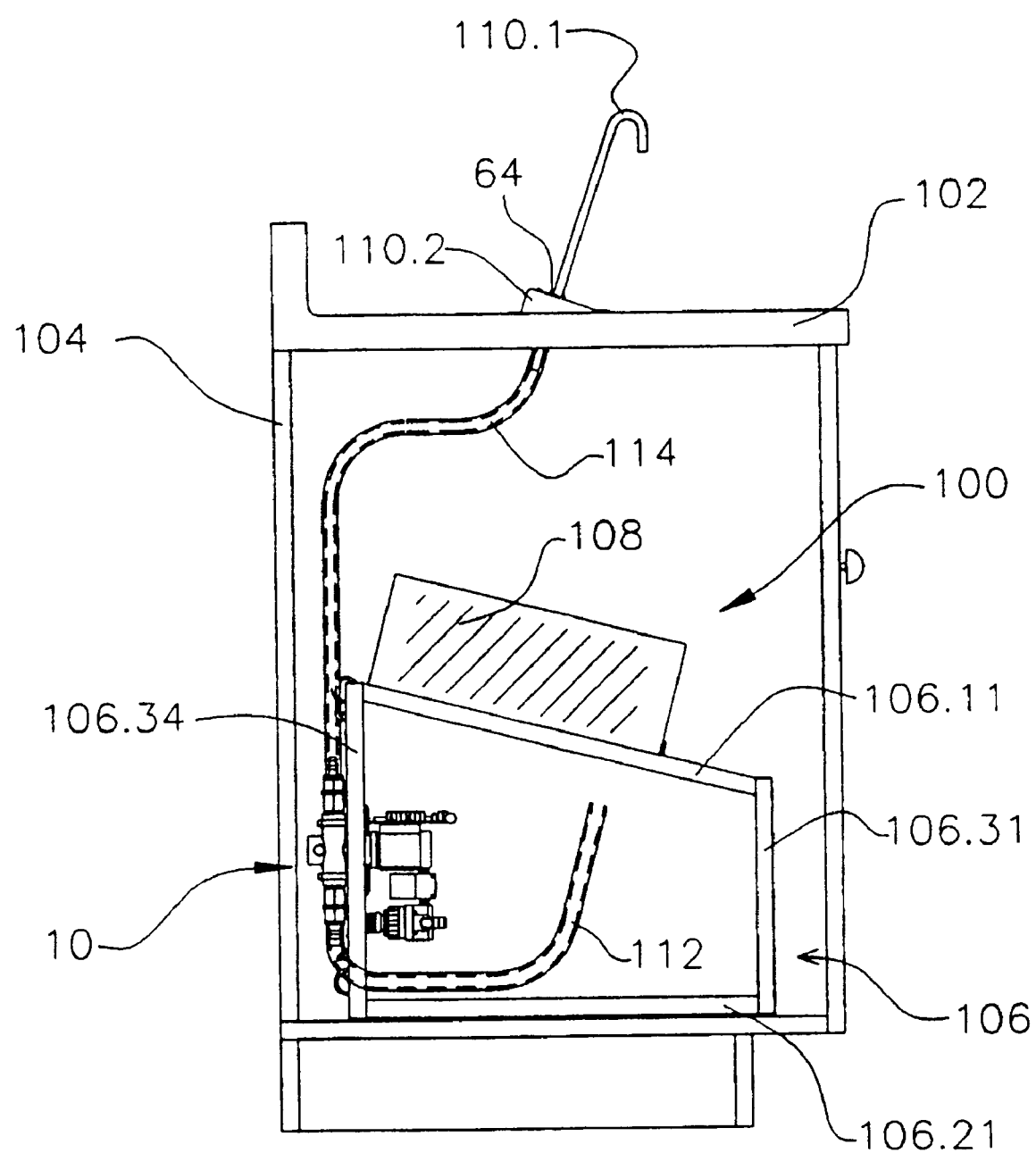
FIG. 3 is a view similar to FIG. 2, this view being taken generally along the line 3—3 in FIG. 1.
Figure 4:
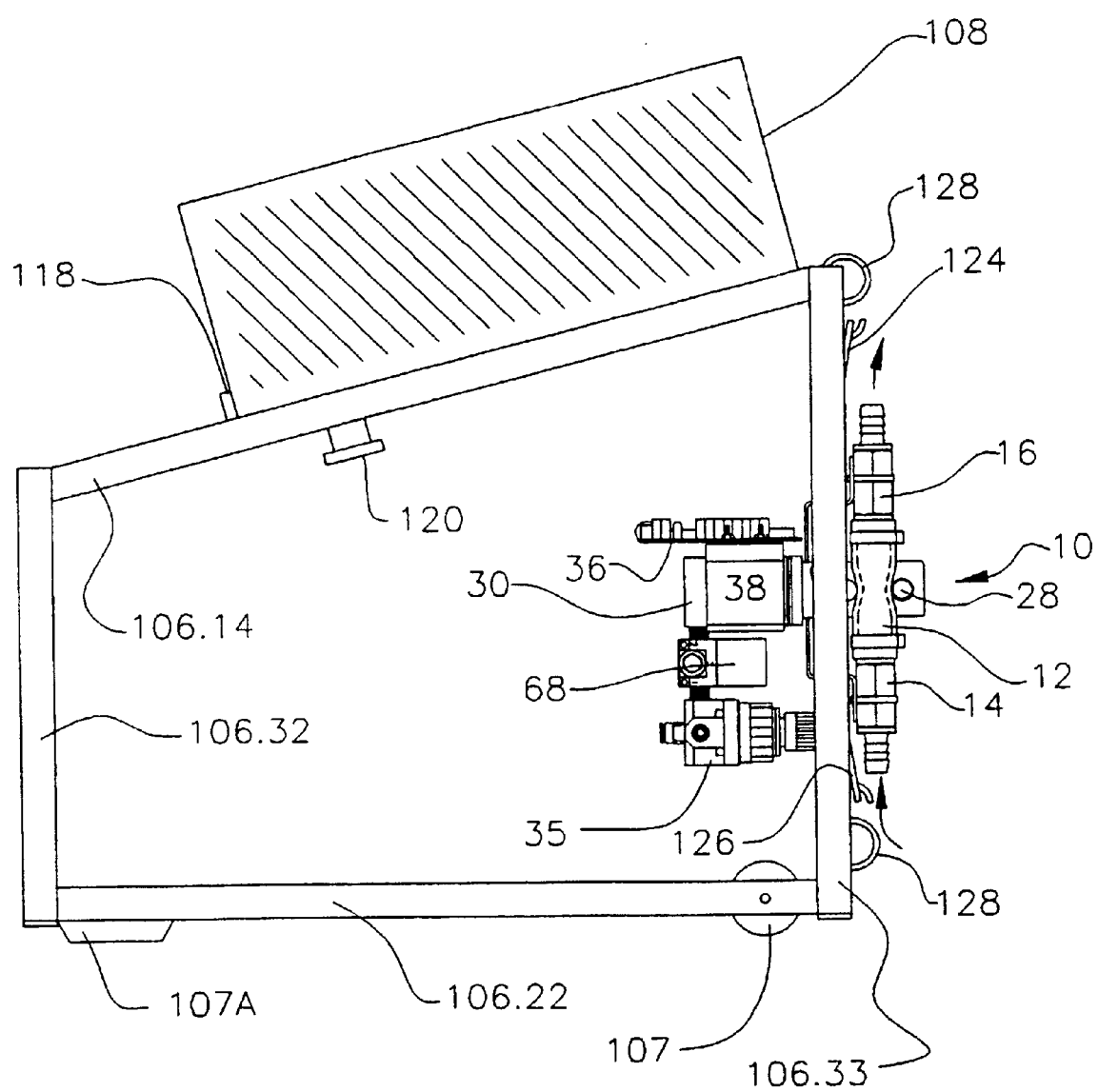
FIG. 4 is an enlarged detail view of the structure shown in FIG. 2, and illustrates the check valve-compressive center section—check valve pump of this invention.
Figure 4A:
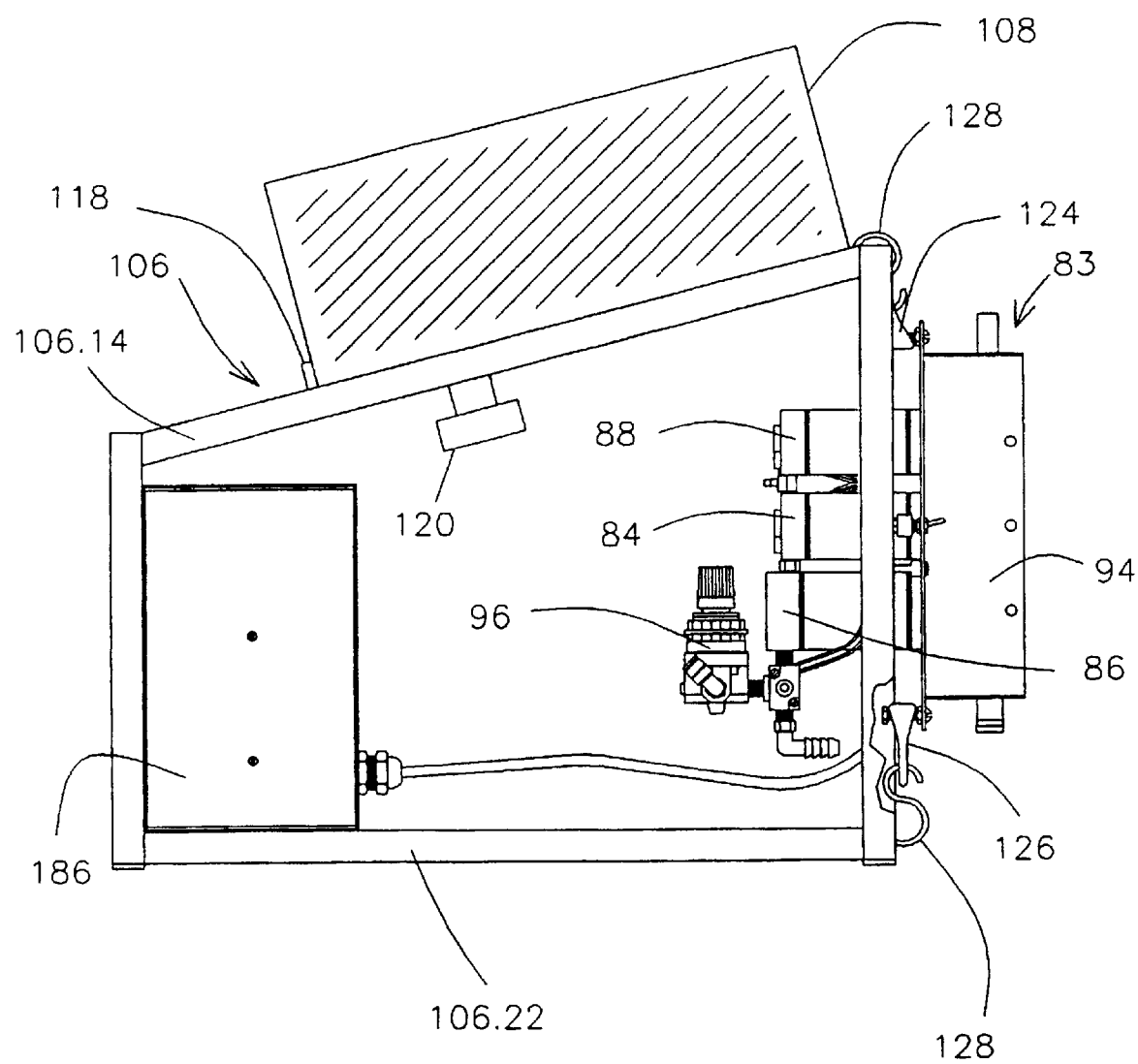
FIG. 4A is a view similar to FIG. 4 but illustrates the condiment dispenser with the three element pump of the type shown in co-pending application Ser. No. PCT/US98/00958 filed on Jan. 16, 1997, herein referred to as a pump with three actuating assemblies which act upon a pump tube.
Figure 5:
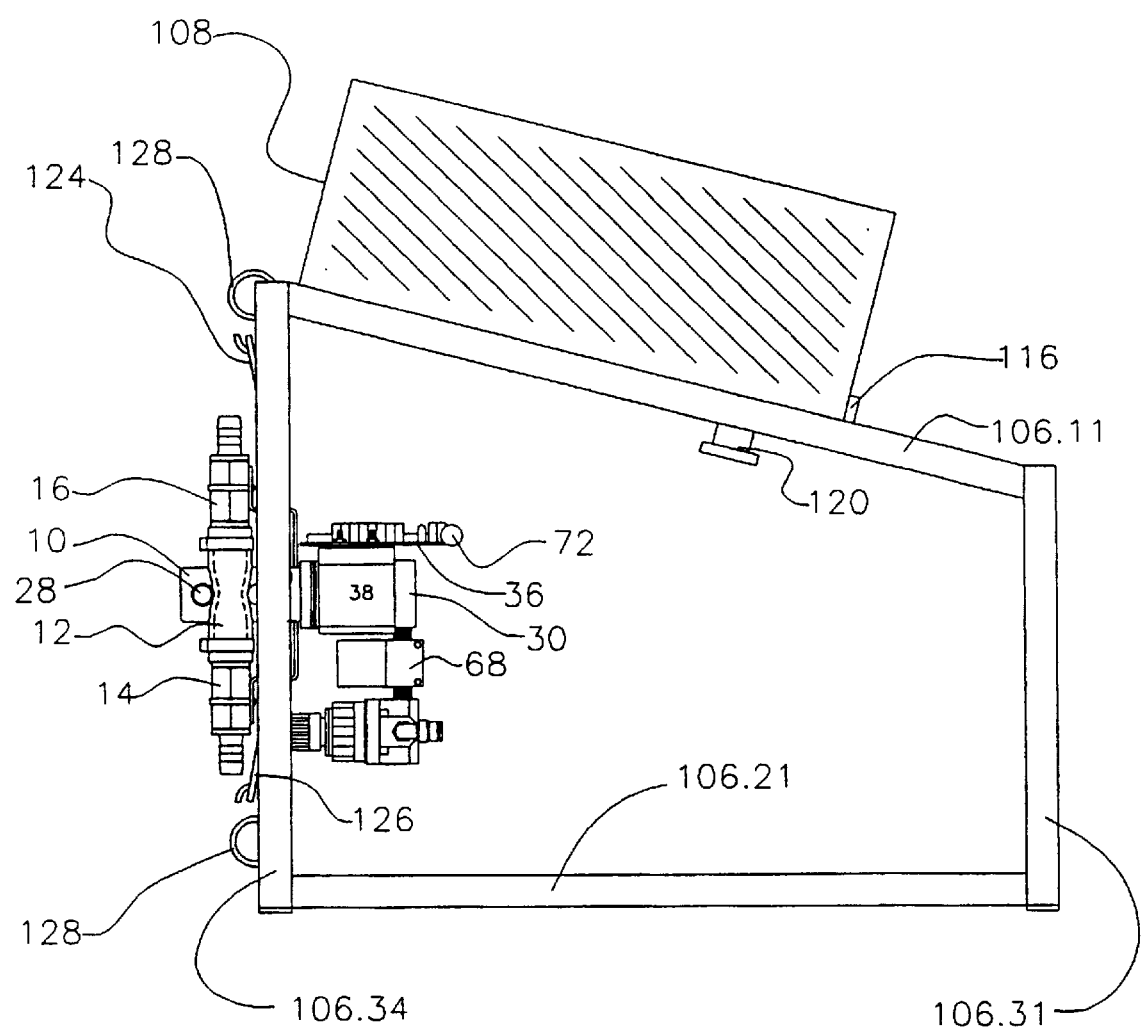
FIG. 5 is a view showing an enlarged portion of FIG. 3
Figure 5A:
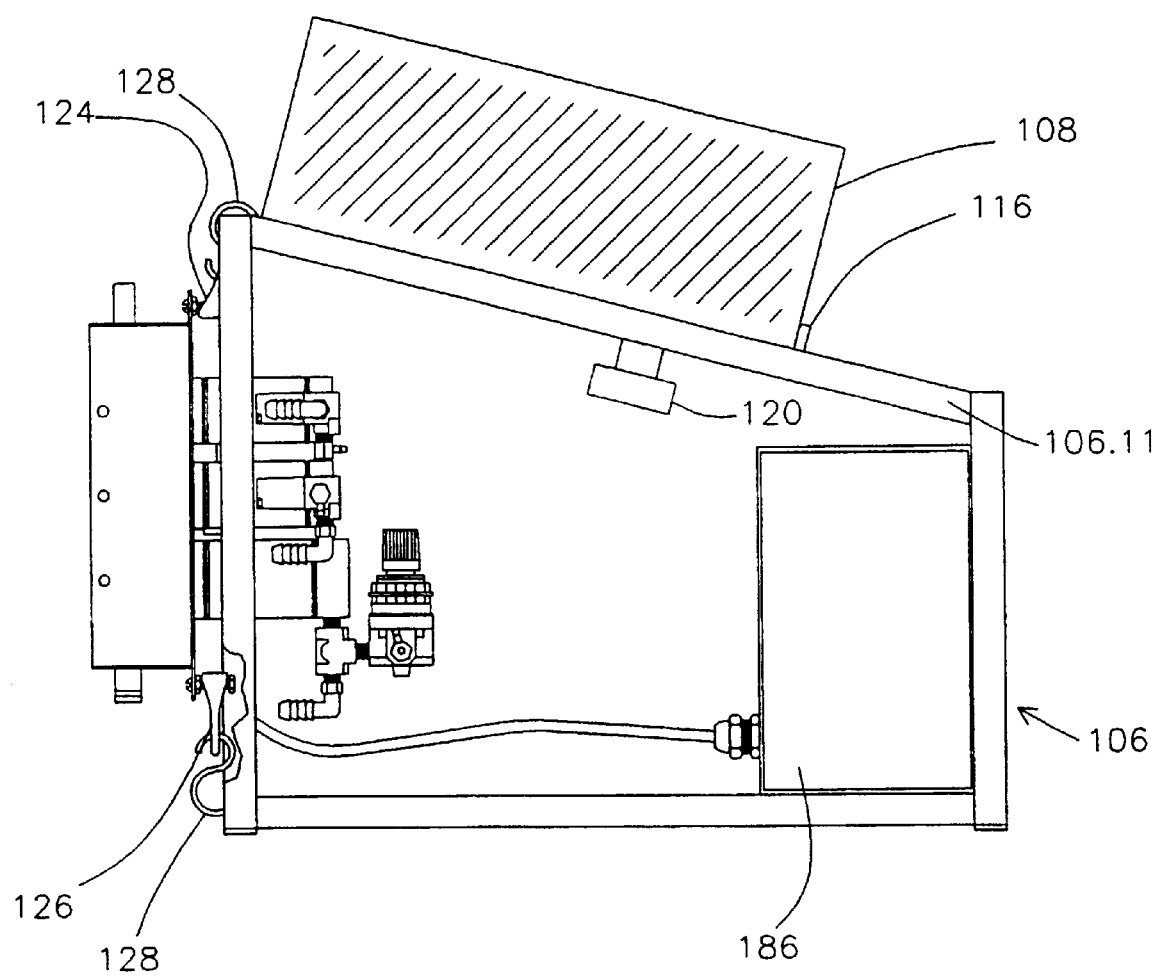
FIG. 5A is a view similar to FIG. 5 but showing a pump with three actuating assemblies.
Figure 9:
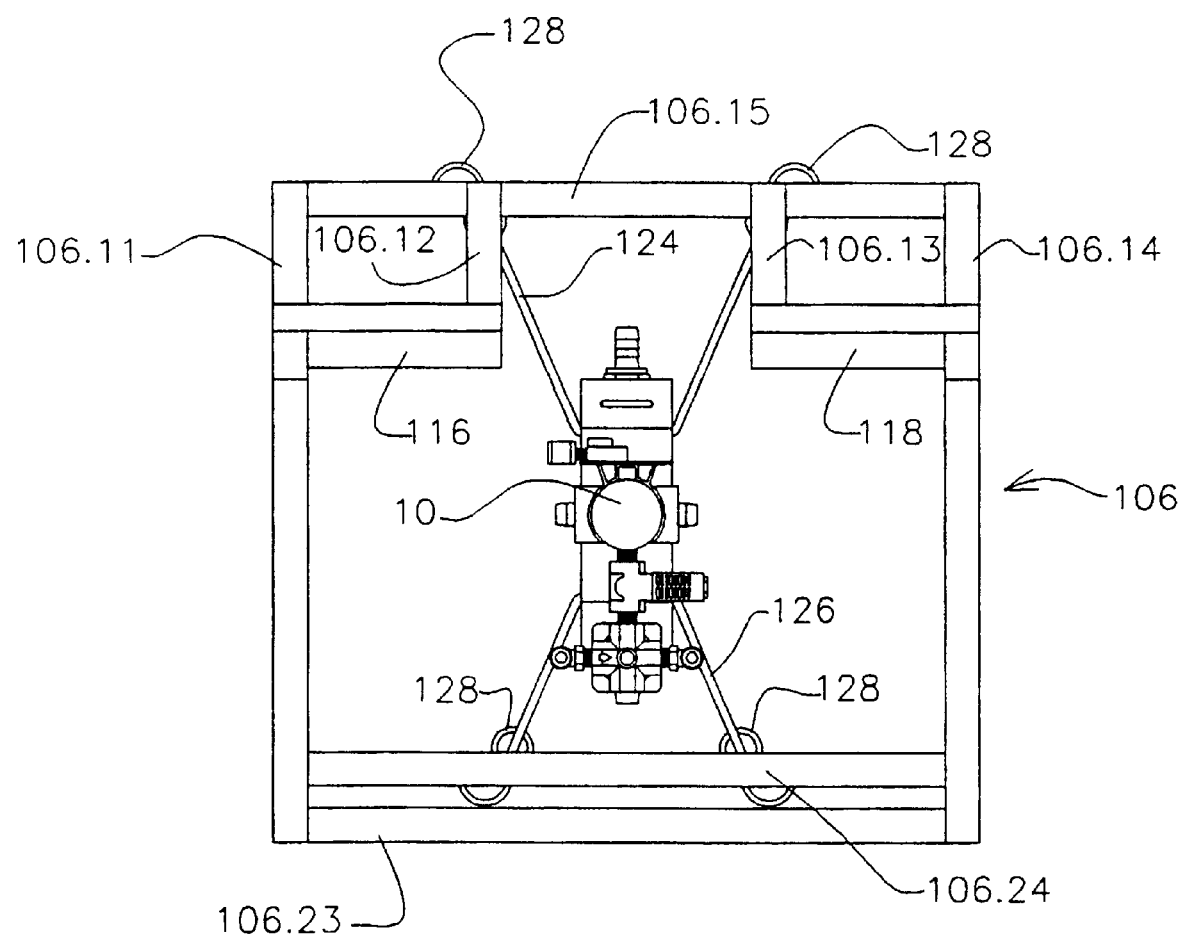
FIG. 9 is a view similar to FIG. 8 but showing the metal frame without the condiment box mounted thereon.
Figure 9A:
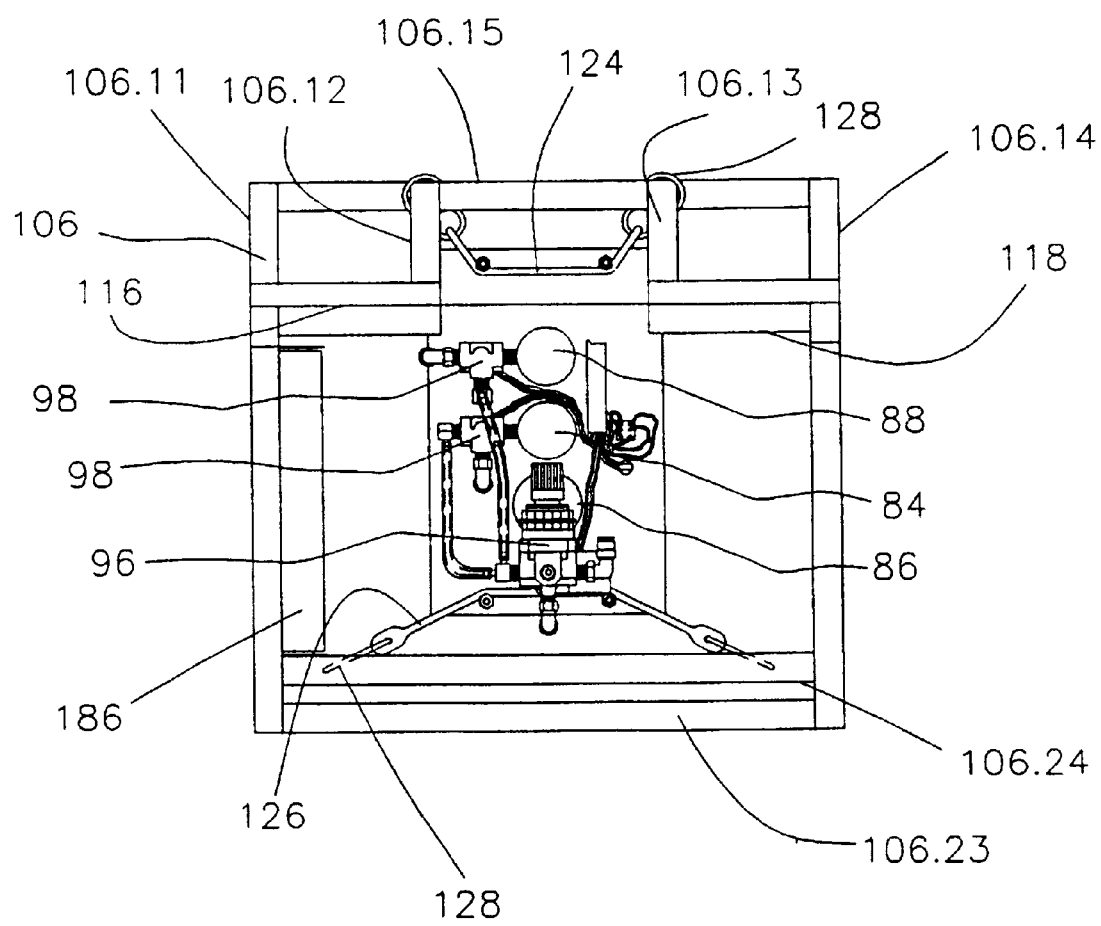
FIG. 9A is a view similar to FIG. 9 but showing a pump with three actuating assemblies.
Figure 10:
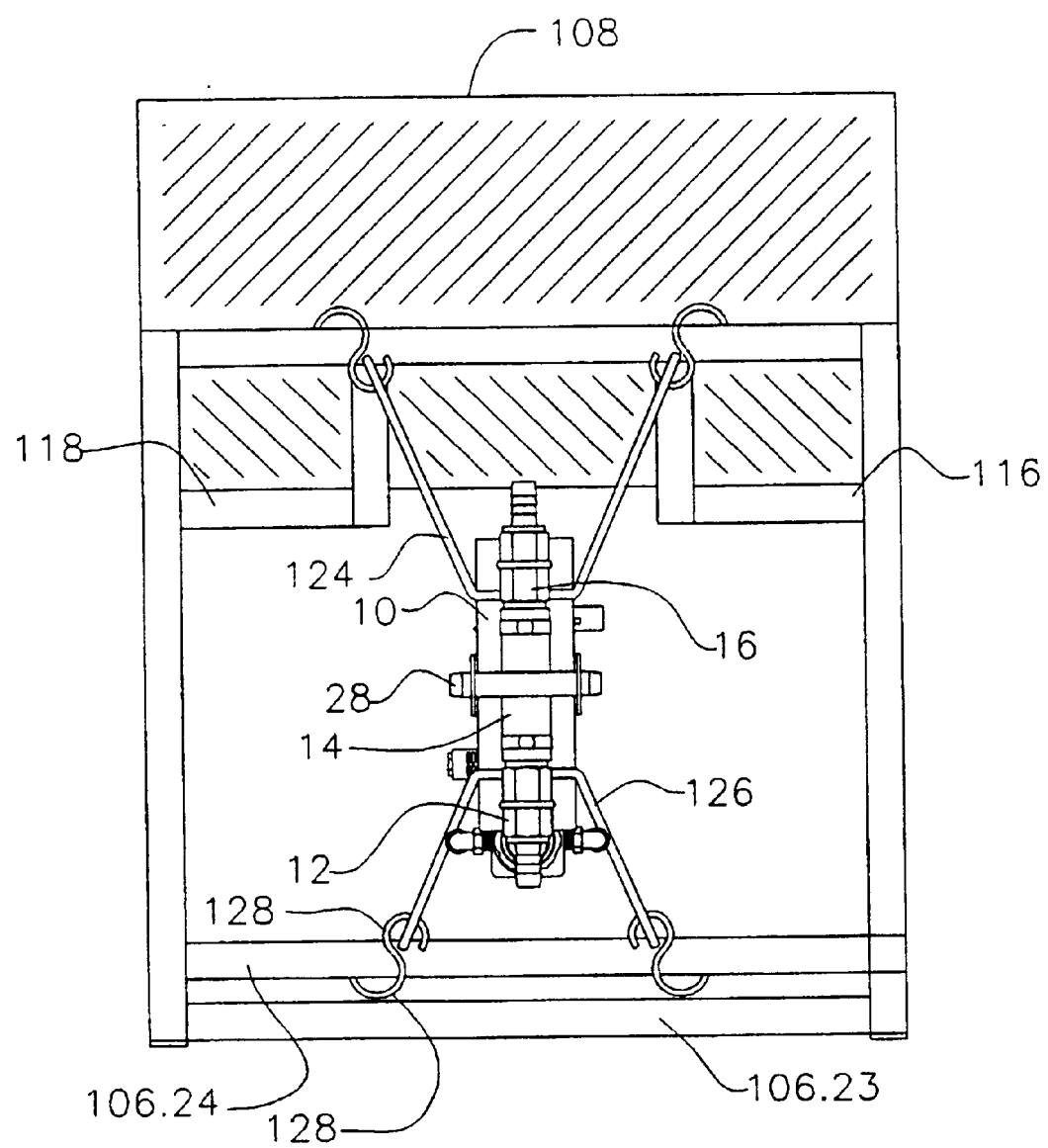
FIG. 10 is a back view of the structure shown in FIG. 8.
Figure 10A:
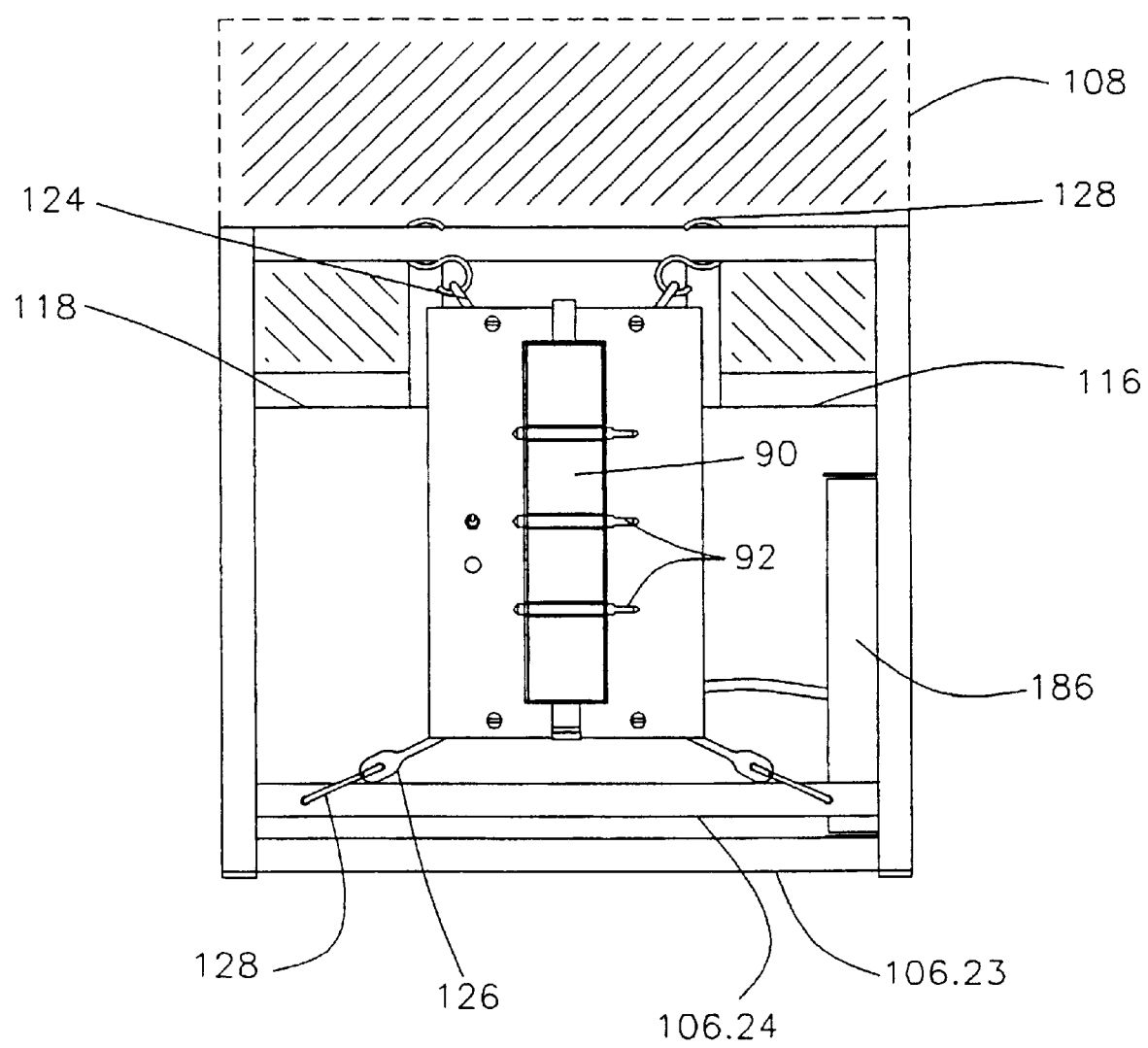
FIG. 10A is a back view of the structure shown in FIG. 8A.
Figure 11:
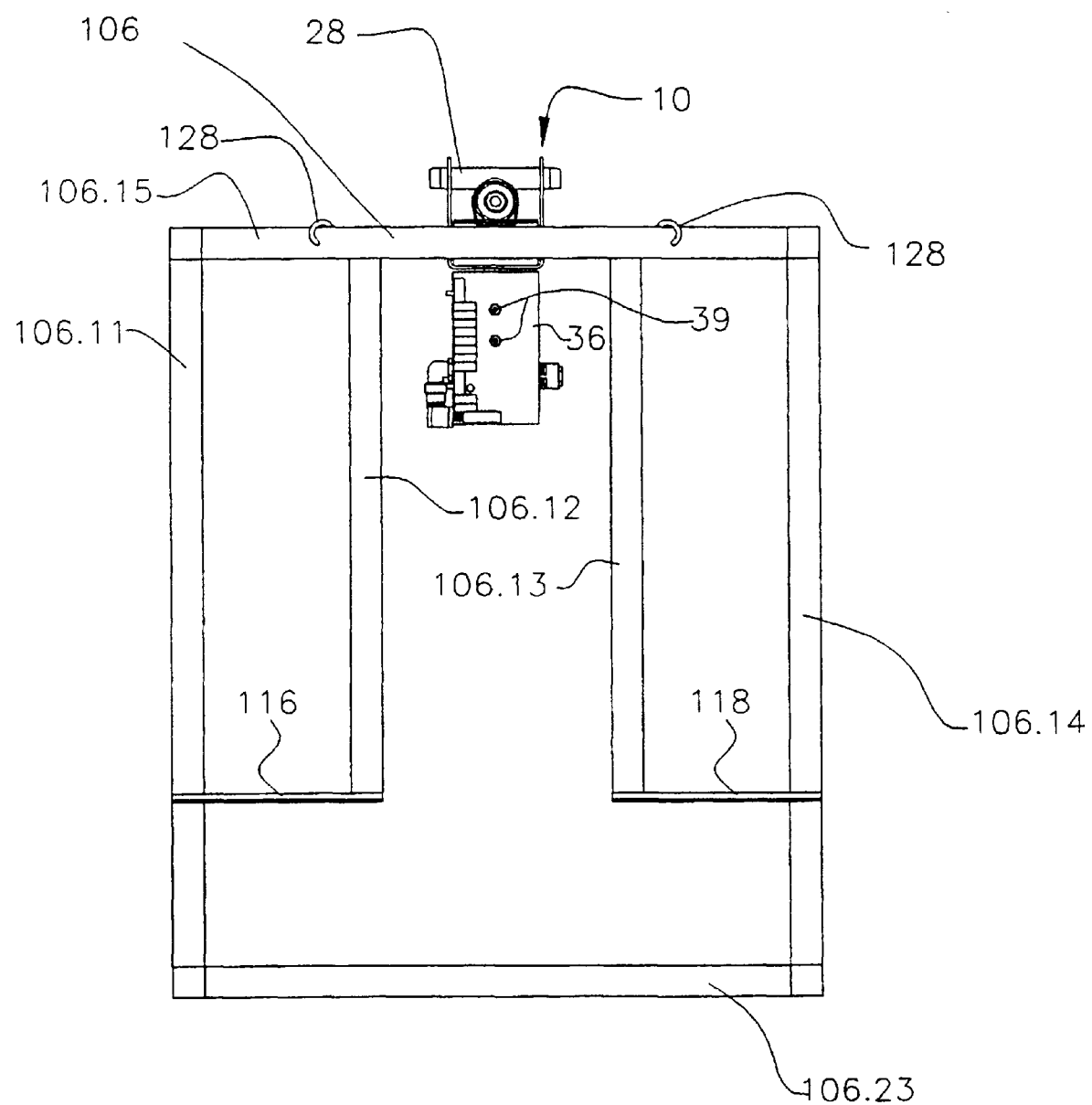
FIG. 11 is a top view of the structure shown in FIG. 9.
Figure 11A:
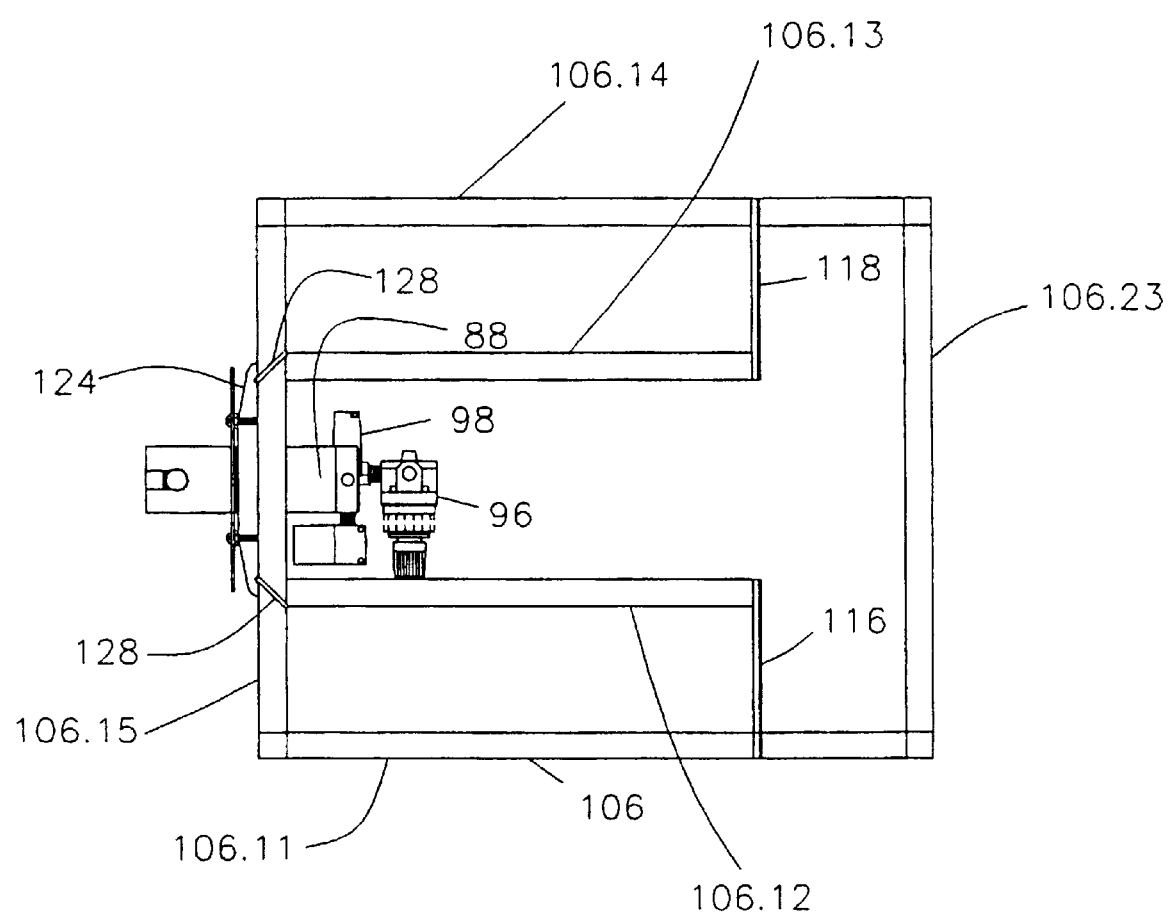
FIG. 11A is a top view of the structure shown in FIG. 9A.

Another novel feature of the present invention consists of a self serve condiment dispenser system configured for use in the dining or public areas of a restaurant or food service establishment. A first embodiment of a dispenser system is indicated generally at 100 in FIGS. 2 and 3, and is primarily intended for placement under a serving counter 102 and/or in a cabinet 104 such as is typically found in most food serving establishments. The system generally consists of a mount frame 106, typically constructed of welded metal rectangular tubes, a dispensing pump 10 mounted to the frame, a bulk supply 108 of the condiment to be dispensed, a point of dispense device or presentation fixture, which is indicated generally at 110, and interconnection resilient flexible tubing 112, 114. The mount frame of this embodiment receives a condiment bag within a box, and is generally rectangular in shape as can best be seen from FIGS. 4, 9 and 11. It is uniquely provided with a slanted upper surface formed by top tubes 106.11, 106.12, 106.13 and 106.14, with an angle from the horizontal of approximately 30 degrees. In addition to the angled top tubes, the mount frame includes a transverse top tube 106.15, bottom side and transverse tubes 106.21–24, and four corner vertical tubes 106.31–34. The frame contains two cleat stops 116, 118 on the slanted top surface. These rails 106.1 and cleats 116, 118 serve as a stable and secure mounting surface for a bulk supply of condiment which generally consists of a Bag-In-Box package (BIB). The Bag-In-Box consists of an outer corrugated box 108, and a flexible laminated film pillow-like inner bag (not shown) containing the liquid condiment. The bag is provided with a fitment or spout 120 which typically can be exposed through a slot or flap on one of the large side surfaces of the box. These packages are commercially available and are widely utilized for packaging liquid products of all types and are generally the package of choice for beverage syrups. Because of the wide use of BIB packages in restaurant environments, they are the dominant choice for packaging bulk condiments for automated dispensing.

The unique slanted upper surface is important in promoting the flexible bag to completely empty of condiment. Empirical tests have shown that BIB units placed at an angle as here disclosed are more likely to empty completely as compared with BIB units where the large surface is placed flat. Thus, the slanted surface mount promotes economy and efficiency of condiment utilization.

Because the BIB mount frame of the self serve dispenser embodiment presently under discussion is generally intended to be placed under a counter, several unique provisions are made in the design of the frame to facilitate the removal of empty BIB packages and the installation of new ones. First, the BIB mount surface is uniquely elevated away from the bottom surface of the cabinet, allowing easy access to the under surface of the BIB package for connection of the BIB spout 120 to the connector 122 on the end of feed tube 112. Second, the slanted BIB mount surface is uniquely slanted toward the front of the cabinet, improving the ergonomics of the BIB package installation and removal. Third, the BIB frame can be equipped with simple inboard mounted rubber or plastic wheels 107 mounted toward the back of the frame, one on each side, and smooth plastic slide strips or skids 107A along the bottom surfaces of each side frame rail 106.21, 106.22. This combination allows easy partial withdrawal and reinsertion of the frame from the cabinet, thus greatly improving access.

Mounted in a generally vertical orientation, a pump unit is novelly attached to the rear surface of the BIB mount frame. The pump used may be the three element linear peristaltic pump herein referenced, or the dual check valve design herein described. The choice of pump is primarily a function of the type of condiment to be dispensed. Any condiment substantially free of entrained particulates may be effectively pumped by the dual check valve design 10, and this design is substantially less expensive than the three element design. In the case where particulated or chunky food products are to be dispensed, the three element, active valve, linear peristaltic design is the pump of choice.

Regardless of the pump selected, it is mounted to the BIB frame in a unique and beneficial manner. In either case, the pump is captured by and suspended from upper and lower stretched rubber or rubber-like straps, or hold-downs 124, 126, also commonly known as bungee cords. This mounting method is simple, inexpensive and durable. Moreover, this method serves to isolate the pump (of either species) from the BIB mount frame thus dramatically reducing the transmission of sound generated by the pneumatically operated pump into the frame and hence into the cabinet, counter or mount surface. The sound reduction gained from the use of this mount method is dramatic. For example, using the dual check valve pump, sound pressure at 36 inches from the pump is reduced from 62 dB when the pump is hard mounted to the frame, to 51 dB when the pump is mounted in the prescribed manner. Each end of each bungee cord is provided with an S-hook. The rails 106.15 and 106.24 are each provided with suitable spaced apart apertures for the reception of one end of each of the S-hooks 128.

The condiment in the BIB is introduced into the pump using a connector 122 which mates with the fitment 120 of the BIB. This connector is variably referred to as a probe, quick-connect-disconnect fitting, or hookup valve. The BIB connector is attached to a flexible pump feed line 112 which connects to the infeed of the pump. On the outfeed of the pump, a flexible tube or hose 114 conducts the condiment to the point of dispense. When within a few feet of the pump, the fluid flow pathway of the condiment dispensing system is completed by direct hookup of the pump outfeed tube to the presentation fixture 110. The presentation fixture at the point of dispense may take on an enormous number of variations, one typical example being pictured in FIGS. 1–3. The presentation fixture is required to be sanitary in construction and is herein provided for as being of stainless steel construction with one continuous flow tube from point of fluid connection to point of dispense.

Figure 17:
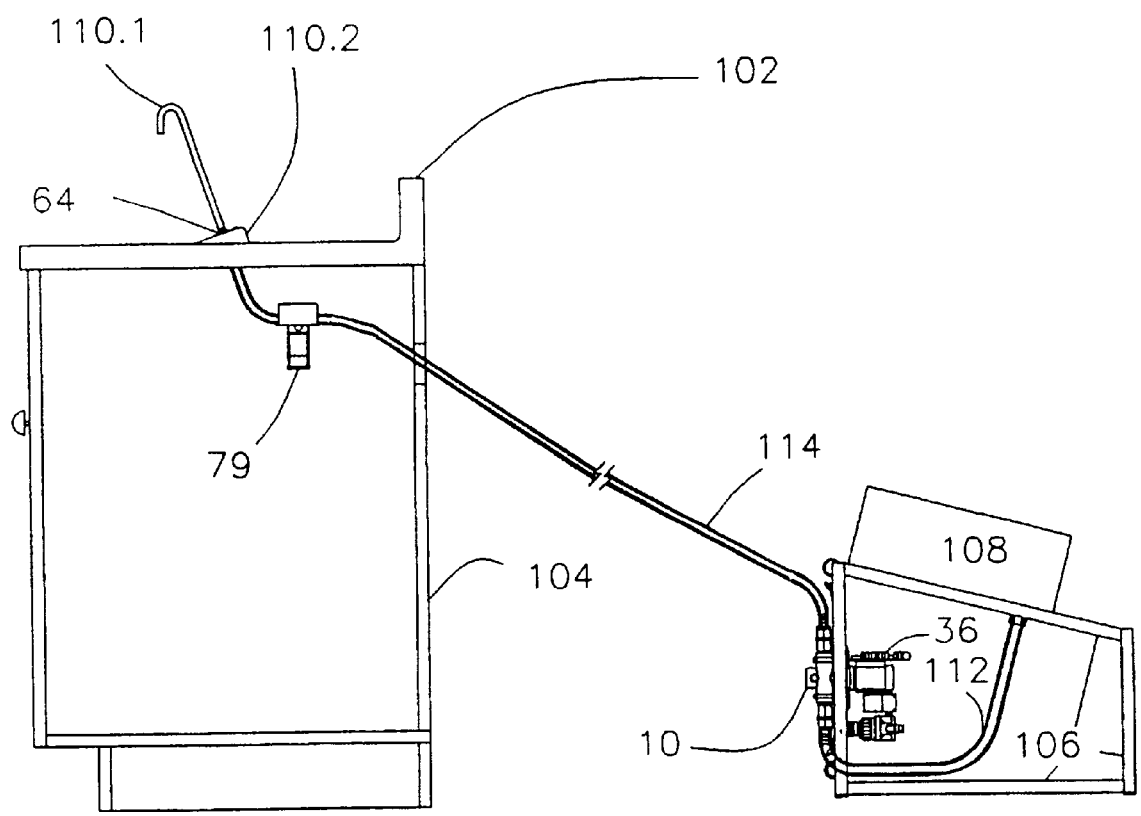
FIG. 17 is a view showing a condiment dispenser mounted remotely from the countertop which receives the point of dispense devices.

When the point of dispense presentation fixture is more than a few feet removed from the pump as shown in FIG. 17, a positive shut-off device 78 is required to be positioned locally at or near the fixture in order to effect a clean and rapid cut-off of condiment flow which is substantially free of ooze or drip. It is important to note that a suitable electronic drive signal to operate such a shut-off device is uniquely provided for in each embodiment of the condiment dispense systems herein described.

The self serve system presently under discussion is completed by a power hookup and by the wiring of a start switch 130 into the electronic control card as previously described. The start or run switch 130 is typically a mechanical unit located as part of the presentation fixture by may also take many other forms, including the use of an optoelectronic device, a touch activated switch or surface (even including the presentation fixture itself), or an ultrasonic sensor. It should be noted that in instances where the three element linear peristaltic pump is utilized, a condiment dispenser so configured is uniquely capable of pumping back briefly at the end of a dispensing even. This reverse flow pumping allows the pump to be separated from the point of dispense fixture by a distance of 10 to 20 feet, without the use of a positive shut-off device, while still achieving a rapid drip free, ooze free cut-off, depending upon the particular condiment being pumped. Where applicable, this novel capability allows a simplified fluid flow pathway which is free of product drip or ooze even at the separation distances described.

Regardless of the pump species utilized in the self serve or dining room embodiment presently being described, the system is particularly and novelly suited to rapid and thorough cleaning and sanitizing in situ. By example, when equipped with the dual check valve pump, a ketchup filled system with a 30 inch infeed tube and a 36 inch outfeed tube can be shown to be free visually of ketchup after through pumping (no recirculation) of less than three quarts of warm or hot water. This very low liquid cleaning volume capability is a function of several unique design factors including the simple straight through design of the pump, which is free of trapping areas, crevices, or bends or turns; the relative high frequency of pump operation, which is typically on the order of 6 to 9 Hz; and the stop-start flow pattern resultant from the intermittent flow characteristic of the pump, which results in an aggressive washing machine like mechanical cleaning action. Even with condiments with high lipids content such as mayonnaise, through pumping with three quarts of a warm water and mild detergent solution followed by a through pump rinse with three quarts of a bacteria killing sanitizer such as a low concentration chlorine bleach and water solution, followed by a through pump with three quarts of clear water rinse will result in a clean and sanitized system suitable for re-use with edible liquid condiments. When the three element pump is utilized essentially the same results are achieved with a cleaning sequence using less than four quarts of liquid at each step. The increase in cleaning liquid volume is due only to the somewhat larger infeed and outfeed lines typically used with this pump species.

More advanced electronics features uniquely enhance the utility and value of the self serve system presently being described. For example, the size, scale and public traffic frequency of restaurants and food service establishments of all types varies greatly, one to the next. In many cases, it is economically desirable to utilize only one condiment dispensing system to service two presentation fixtures located at separate areas within an establishment. The unique provision for electronically controlled and integrated multipoint dispensing allows this to be readily and inexpensively implemented.

Figure 19:
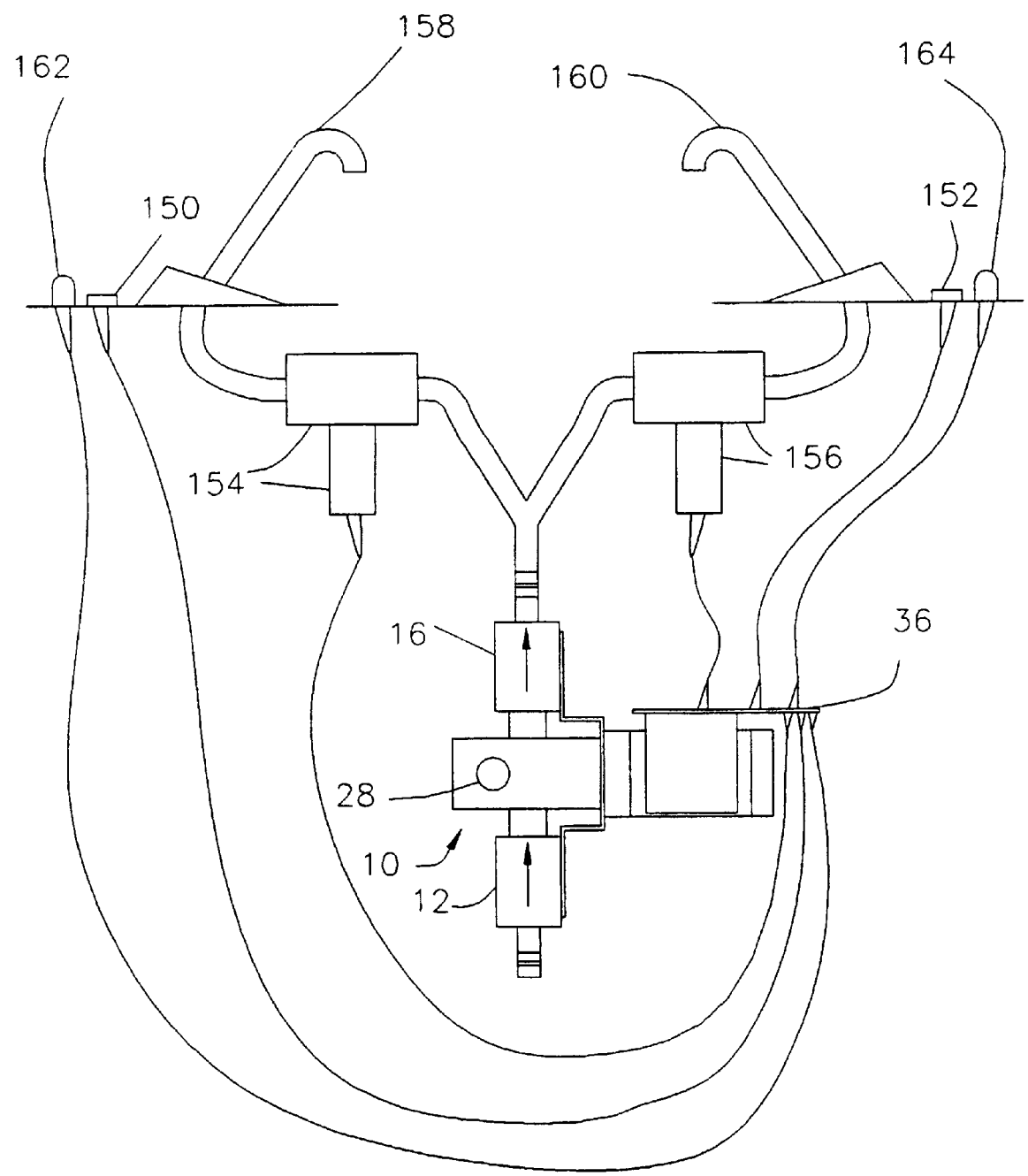
FIG. 19 illustrates how the pump of FIGS. 12 and 13 may be interconnected with two separate presentation fixtures.

In the embodiment of the design of the present invention shown in FIG. 19, first and second start inputs 150, 152 are available, each input being electronically linked to a positive shut-off output driver. This feature allows a single pump 10 to service more than one location. In addition, there are first and second positive shut-off devices and first and second fixtures 158, 160 respectively. In operation, the first start input to arrive electronically locks out or disables all other inputs. Thus, operation of the first start input 150 initiates pumping and opens the first remotely located positive shut-off device 154, thus allowing condiment flow only through the presentation fixtures 158 at that location. If the dispenser system is configured in a dose mode, the correct dose is delivered at the first location and all other dispensing points or locations remain locked out until the dose at the first location is completed. If the dispenser system is configured in an on demand mode, flow at the first-in location continues until the start switch is released, and all other locations remain locked out until demand flow ceases. It is important to understand that any start input switch closure at any other location is ignored during dispensing at the first active location. Equally important, any start input switch which is closed at any other location at the end of dispensing at the first active location novelly does not result in condiment flow at that location since the person at that location might have no expectation that flow was about to begin. Thus, a surprise flow condition is uniquely avoided by the design of the electronics such that it is necessary to release or open any start switch which has been previously closed while locked out by dispensing at another location.

Also uniquely, the use of an electronically addressed and actuated positive shut-off device, such as 154 or 156, at each point of dispense indicated by fixtures 158 and 160, respectively, such that only one shut-off can be opened at any given time, assures that a correct dose or flow rate is always delivered since division of the pump's flow to more than one location cannot occur.

Because the condiment dispensing system of the present invention is designed to provide flow at only one location at a time, an output driver for an LED lamp 162 and 164, respectively, is provided for each start input provided. Whenever a particular start input is active, the LED driver associated with every other start input is active. Thus, if implemented, all other presentation locations can be equipped with a visual indication via an associated LED lamp to show that the system is busy. This is helpful to a patron wishing to utilize the dispenser but finding it inoperable. The individual need only wait for the busy LED to go out in order to gain access to the system.

In many restaurants, it is difficult to monitor the status of equipment placed in the dining room or public service areas, either because of the size or layout of the establishment, or because the background noise level may make local audible alarms or warnings difficult to hear. The features of the electronic controller of the automated condiment dispensing system of the present invention offer unique solution to these problems, by allowing remote monitoring of dispenser status. In any of the embodiments of the condiment dispenser systems herein disclosed, the electronic controller can provide diagnostic information. The systems herein disclosed have utilities requirements consisting of compressed gas at a specified minimum pressure, and electric power. The availability of correct gas pressure can be monitored by a suitable pressure switch, and an input is provided to monitor the status of the pressure switch when the system is so configured.

For remote transmission of information to a convenient central location within the restaurant, the dispenser electronic controller may be uniquely equipped with an Remote Information Port 166 (RIP). This port consists of an optically isolated output which may be used to establish a two wire current or voltage loop to a Remote Information Module (RIM). In operation the RIP transmits a steady state DC signal to the RIM as long as correct compressed gas pressure and power are available. This constitutes as on line or service ready status. Loss of power or gas pressure causes the signal to drop out completely. The loss of signal at the RIM for a period greater than two second will continue, by definition, a utilities failure at that particular dispenser.

The same two wire RIP can transmit an out of condiment product condition to the RIM. The electronic controller of any of the disclosed dispensers can be provided with an input to monitor a condiment product availability device. When lack of condiment is detected and signaled into the dispenser controller, the RIP signal pair is pulsated at a frequency of approximately one Hz. This constitutes a distinct signature condition which can be detected by the RIM. When utilized, any of the utility or empty BIB faults inhibit the function of the dispenser. If power is available, and a status LED is located at the presentation fixture or other form of point of dispense, the LED is caused to pulse rapidly, providing local indication of a malfunction.

Another very important capability and benefit uniquely provided by the disclosed condiment dispensers concerns the ability to predict an empty BIB condition before customer service is interrupted. This is difficult to do without annunciation of a low BIB status at some control monitor location. The RIM device previously mentioned serves this purpose.

In operation, the RIP data loop established with the RIM provides consumption data allowing prediction of an imminent empty BIB condition. That is, the same two wire connection providing diagnostics and empty BIB status can also transmit consumption data. To understand how this is accomplished, recall that both pumps defined by this and the referenced specification are positive displacement devices and thus capable of displacing a known volume of condiment with each pump cycle. It is also true that bulk condiments supplied in BIB packages are filled with a precisely defined amount of product. With these two conditions, it is readily apparent that BIB product usage can be traced and depletion predicted.

In practice, each cycle of the pump produces a 10 millisecond pulse transmission from the RIP to the RIM. This constitutes a unique signal which can be unambiguously decoded by the RIM as a pump cycle event. Thus, by counting cycles generated by a particular dispenser pump with each cycle representing a known volume of condiment, and with the starting weight of the BIB known, an empty BIB condition is readily predictable.

Another unique and important benefit available as a result of the ability of the dispensers of the present invention to provide condiment consumption information, is the ability to provide inventory tracking and re-supply information. This data flow directly from the above described usage tracking link and it can be formatted locally by use of a dedicated microprocessor based inventory data collection terminal (as commonly used in food markets), via a PLC and modern onto a local or wide area network or by formatting in a PC for local use or transmission onto a wide area network.

KITCHEN CONDIMENT DISPENSER SYSTEM

Figure 20:
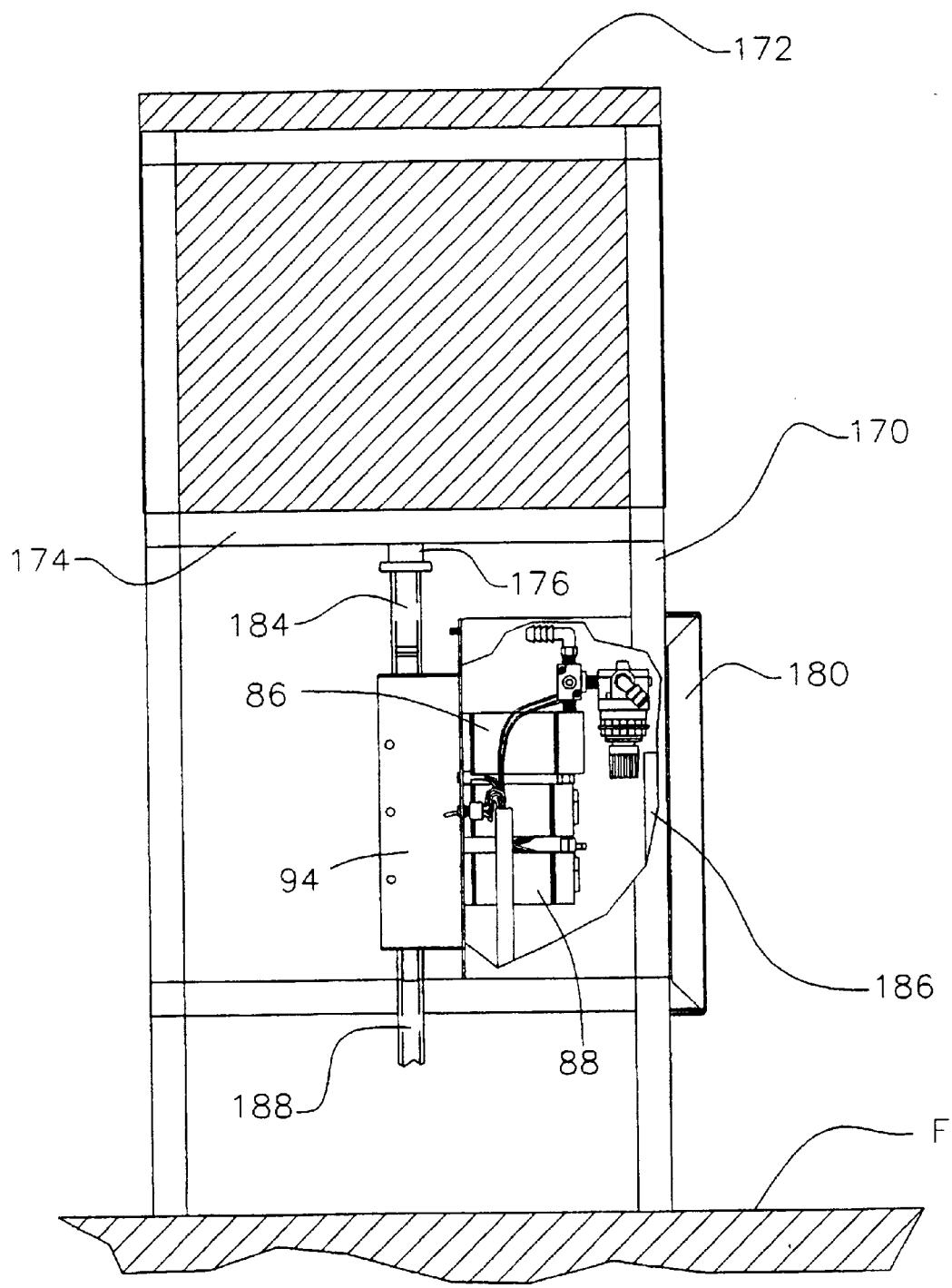
FIG. 20 is a right side view of a kitchen unit with condiment packages mounted thereon.
Figure 21:
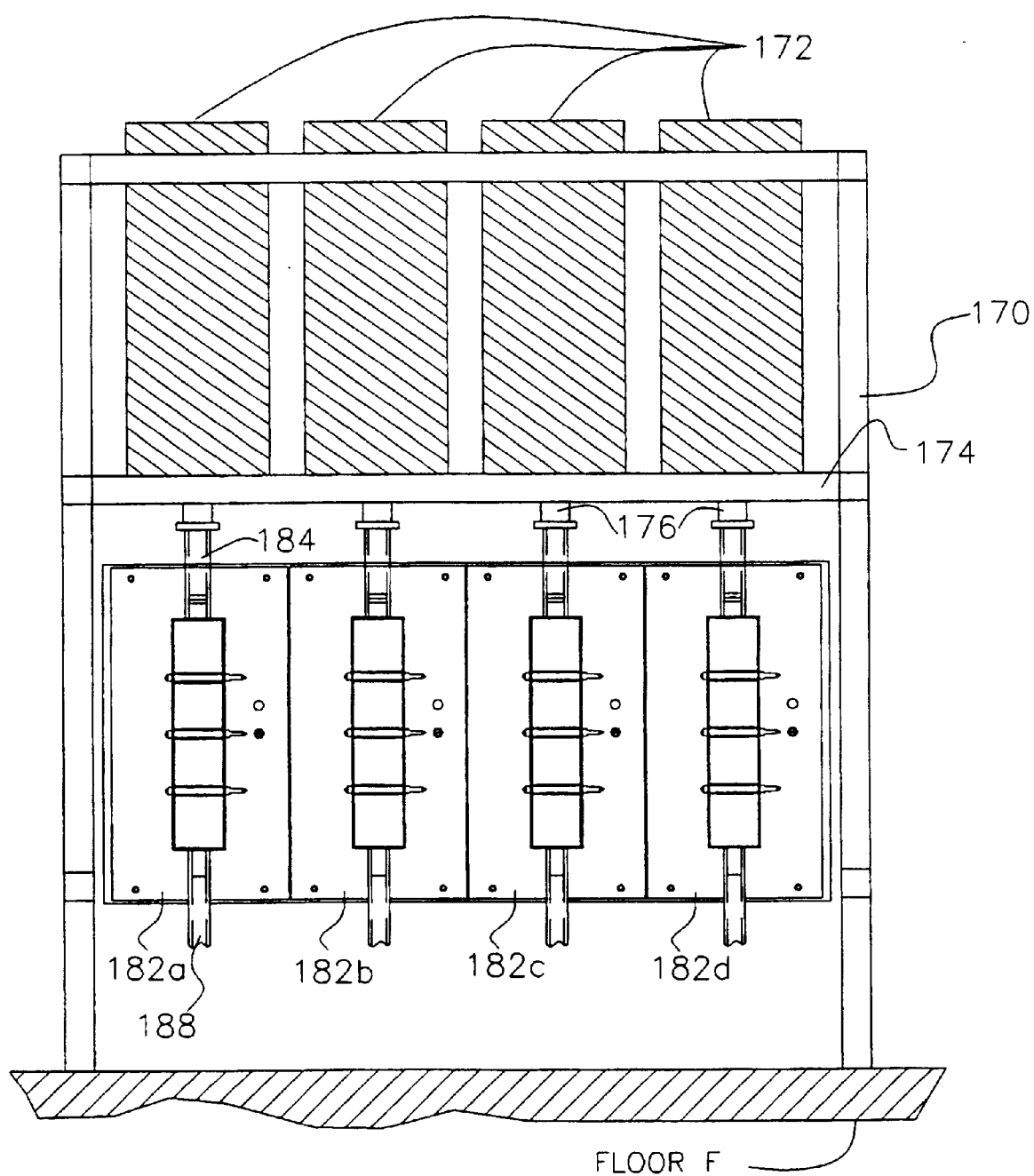
FIG. 21 is a front view of the unit shown in FIG. 20.
Figure 22:
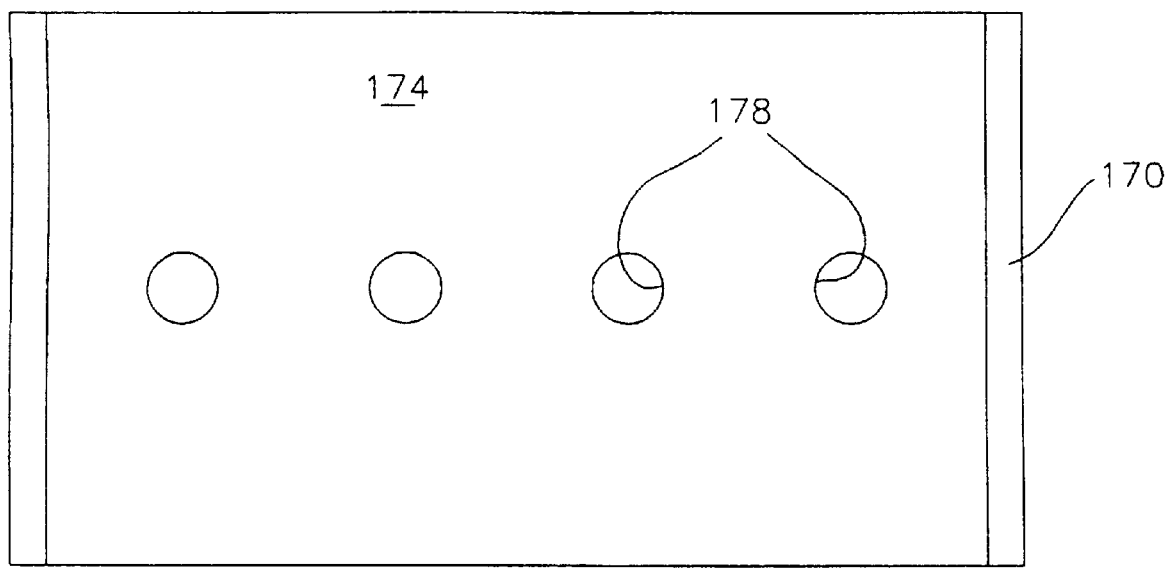
FIG. 22 is a top view of the unit shown in FIGS. 20 and 21.
Figure 23:
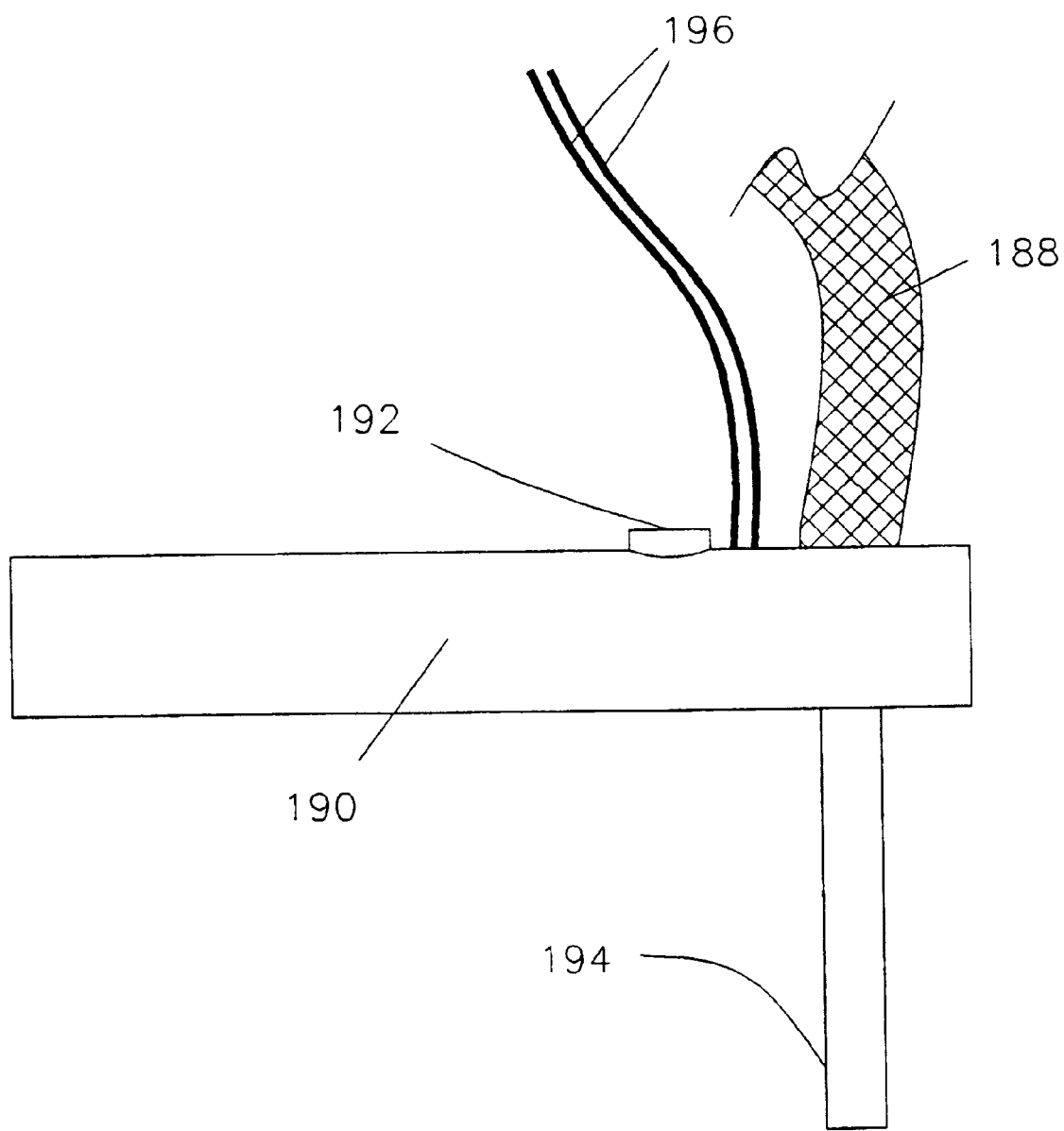
FIG. 23 and 24 illustrate separate styles of condiment dispensing wands, the design shown in FIG. 24 being provided with a positive shut-off device.
Figure 24:
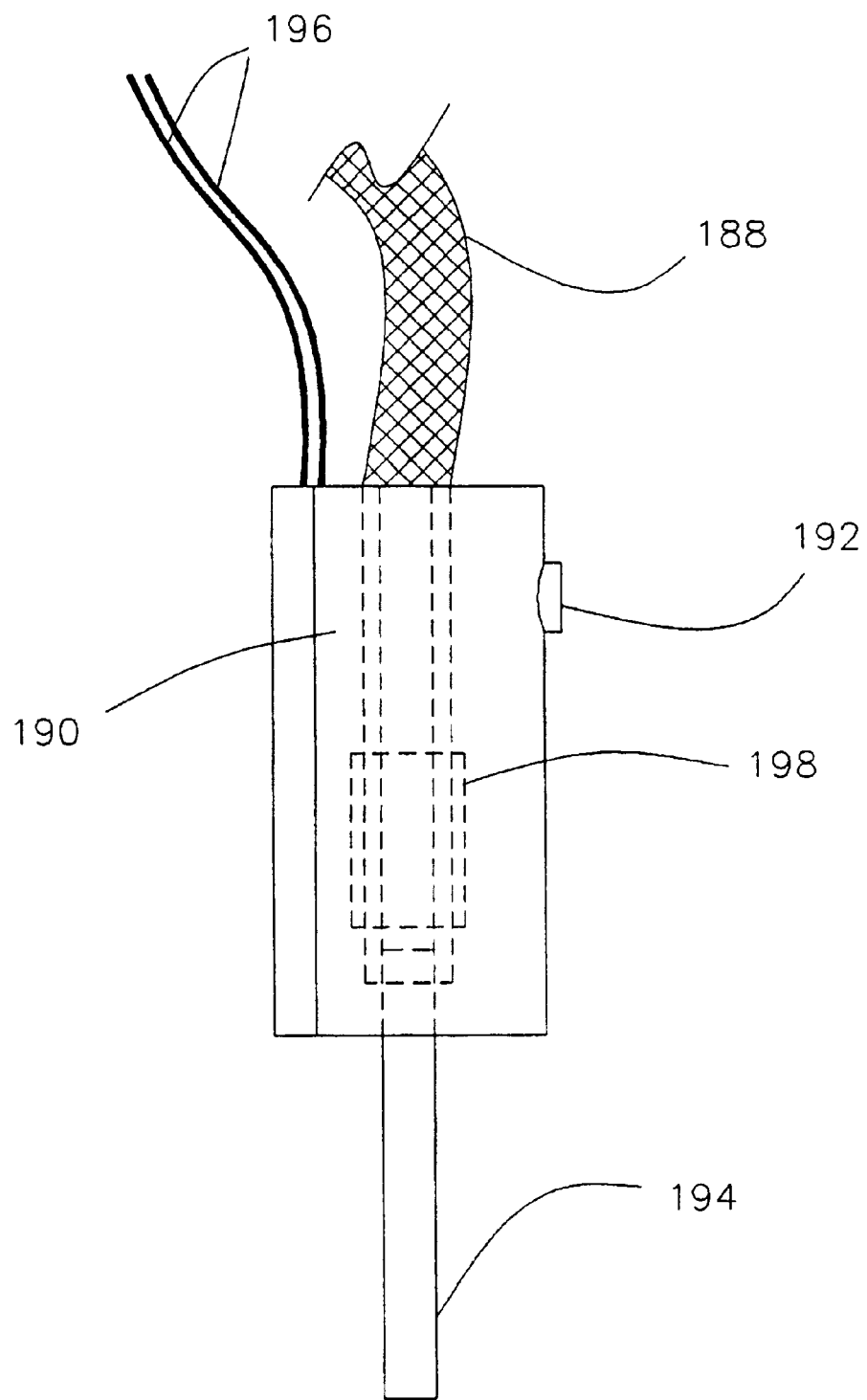

Another novel feature of the present invention consists of a condiment dispense configured for use in the kitchen or food preparation area of restaurants and food service establishments. This second embodiment of a condiment dispenser system is generally indicated by FIGS. 20–22.

The kitchen system generally consists of a compact system frame 170, typically fabricated from stainless steel, the bulk supply of condiments in BIB packages complete with the outer cardboard box 172, the point of dispense device (shown in FIGS. 23–26), and the interconnecting product flow tubing. The system frame is generally rectangular and consists of an upper shelf 174 designed to hold the boxed BIB packages 172, generally on an edge-wise orientation such that each BIB fitment 176 projects downward through a hole 178 (or slot) in the shelf toward the bottom of the stand. The bag within the BIB box 172 is the same as the bag within the BIB box 108, the only difference being the manner in which the box is opened to expose the BIB fitment 120 or 176. While in the application, the condiment bags are shown mounted within an associated box, it is possible to remove the bag from the box and still practice the principles of this invention. Thus the bag may be hung in the manner shown in U.S. Pat. No. 5,366,117, alternatively, the bag may be placed in a cradle as taught in U.S. Pat. No. 5,624,056. Alternatively the condiment container could be something other than a bag, for example a suitable bucket or the like.

Mounted to the system frame below the BIB shelf of the kitchen dispenser is a pump mount enclosure 180. This enclosure is generally fabricated from stainless steel and is gasketed to be generally resistant to the entry of water, cleaning solutions and food products. The pump mount enclosure 180 is mounted in the system frame in such a way as to assure a substantial separation of the bottom of the pump mount enclosure and the floor F in order to assure easy access to the underside of the stand for cleaning of the stand and the floor area occupied by the stand.

The placement of the BIB packages on edge is unique and is particularly intended to allow the stand to be as compact as possible in order to minimize the floor space required for its placement. Also unique is the use of the BIB package while still in its shipping box. When removed from the box, bags of condiment, which typically are in three gallon sizes and weigh approximately 25 pounds, a very difficult to handle, there being no firm surface to grasp or control. Thus, by unique use in the box, the dispenser system of the present invention simplifies and speeds handling and reduces installation and replacement times.

The use of a free standing system frame novelly allows the complete condiment system to be self contained and eliminates the need to place the unit under a table or counter. This greatly improves access and allows greater freedom of placement in restaurants with greatly varied layouts. The pump mount enclosure is uniquely designed with four removable stainless steel dress plates 182 $a$–$d$, allowing modular mounting of one to four condiment pumps of either of the two species herein described. This novel design allows pumps to be added or deleted from a system while assuring the integrity and cleanliness of the pump mount enclosure. It is possible to design stands accommodating two or more pumps, although the 4-position unit illustrated is believed to be the most common variant.

Using the three element pump shown in Appendix A, as an example, the condiment pump can be face mounted on the dress plate with the infeed port up and the outfeed port down. This allows a direct flood feed of the pump from the BIB package located directly above each pump respectively. While the described pumps have robust suction capability, flood feeding speeds priming of condiments of all types and viscosities and enhances discharge flow rates. The juxtaposition of the BIB package directly over the pump uniquely allows the interconnecting infeed tube 184 to be as short as possible, which has the dual benefit of reducing system volume to a minimum and also reducing flow friction to a minimum.

Connected to the outfeed of each pump is a length of outfeed tubing 188. When using the three element pump, the outfeed may uniquely terminate in a point of dispense device (FIG. 23) consisting of a simple handle fixture 190 containing a suitable start switch 192, and a short stainless steel delivery tube 194, the switch being connected to the controller 186 by suitable electrical leads 196. When so configured, condiments of essentially any type may be dispensed in an one demand or dose mode. Uniquely, condiments that can be displaced with the same pump include smooth and chunky condiments such as pumpable pickle relish, special sauces such as Big Mac Sauce and Arch Deluxe Sauce of McDonald's Corporation, thick picante sauces with particulates in excess of 0.375 inches in diameter, and tarter sauces. When terminated by a simple flow tube (no positive shut-off device) the configurable and adjustable pump back (reverse pumping) capability of the three element pump can provide a rapid cut-off of flow, free of drip or ooze, at a distance of up to 15 to 20 feet from the pump discharge port.

The novel ability of the condiment system of the present invention to effectively pump condiments containing large chunks of food materials in high concentration is directly a result of the design of the three element pump, as previously disclosed, but also of the ability of the pump electronic controller to effect a reverse flow capability for cut-off of such condiments at the point of dispense such that a straight through fluid flow pathway free of restrictions or obstructions can be utilized.

A suitable positive shut-off device 198 (shown in phantom lines in FIG. 24) can also be used to cleanly cut-off the flow of chunky or nonhomogeneous liquid condiment products. Unique to this capability, and germane to this specification, is the provision for the positive shut-off device to be actively driven or positively controlled by the pump electronic controller. Also uniquely, when a suitable positive shut-off is used, the three element condiment pump is capable of pumping viscous highly particulated condiments, such as tartar sauce, a distance of at least forty feet from the pump without detectable latency of flow from moment of start switch actuation. By example, at such a distance, the condiment system of the present invention, utilizing the three element pump species, can deliver a one third ounce dose of tarter sauce in less than one second. Also uniquely, when a suitable positive shut-off device is used, the condiment system of the present invention is capable of pumping a smooth condiment such as ketchup, mustard or mayonnaise a distance of at least 100 feet from the pump without detectable delay or latency of flow from the instant of start switch actuation.

The unique ability of the condiment system herein described to pump liquid products over an extensive distance without a bothersome or noticeable delay in the inception of flow upon start switch actuation is a direct consequence of the use of an active or driven shut-off at the remote point of dispense. This is true because, at the end of each dispensing cycle, the shut-off is rapidly electronically closed such that the outfeed pathway to the remote point of dispense cannot decay in pressure. Thus with the next dispensing cycle the pump is not required to pump the outfeed structure up to some pressure where flow ensues, and thus flow occurs on an essentially instantaneous basis upon electronically opening the shut-off.

Figure 25:
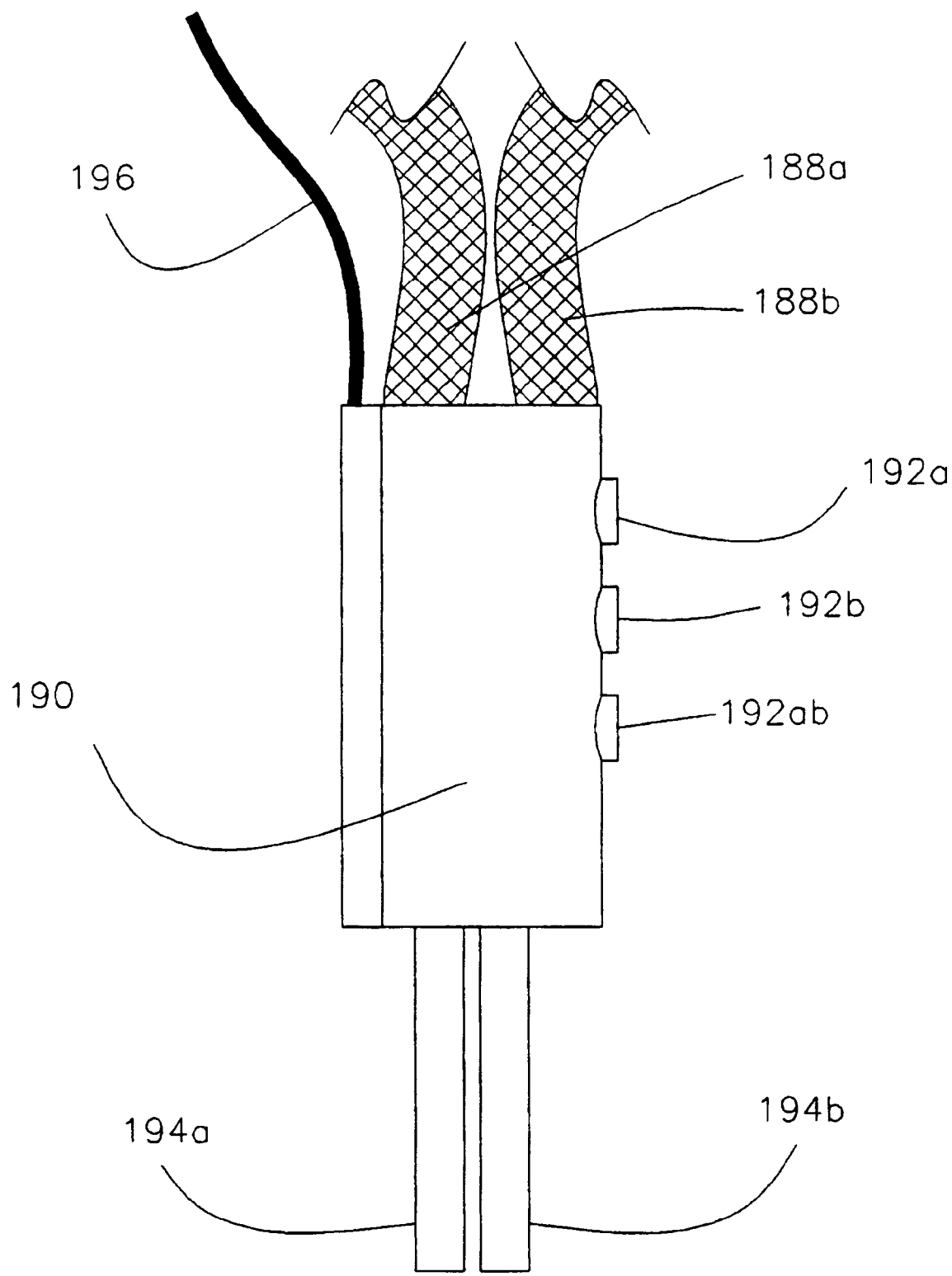
FIG. 25 illustrates a point of dispense condiment wand which can dispense two condiments either individually or at the same time.

The use of electronic controls as elsewhere described allows unique and important capabilities for the kitchen condiment dispenser. For example, it is frequently true that many fast food or quick serve restaurants prepare sandwiches with a variable combination of condiments, the most frequently used being ketchup and mustard. Because the electronic controller of the three element pump has the provision for multiple start inputs and for a slave start output pulse, a dispenser (as shown in FIG. 25) can be readily configured, as desired, to dispense at the point of dispense ketchup only by pressing switch 192A, mustard only by pressing switch 192B, or ketchup and mustard simultaneously by pressing switch 192AB. In this regard, ketchup will be received from an associate condiment supply and pump through flexible hose or tube 188*a*, and mustard will be received through tube 188*b*. Thus, this unique ability to simultaneously dose two or more condiments simultaneously with the touch of only one start switch or button has the effect of greatly compressing the time of dispensing. This time savings is considered to be very important to the speed of sandwich making in many fast food restaurant settings.

Speed of condiment delivery in a kitchen setting is generally considered crucial to efficiency of sandwich assembly. The kitchen system of the present invention, when equipped with the three element condiment pump, is demonstrably and uniquely capable of delivering a one third ounce dose of ketchup at a distance of twenty-five feet from the pump in less than 500 milliseconds.

The kitchen system, as with the self serve system, is capable of being placed into a dose mode whereby a predetermined amount of condiment is accurately delivered at the point of dispense. As with the self serve system, the dose capability of the kitchen system is uniquely designed to be self completing regardless of the point of dispense structure.

As briefly mentioned with regard to the self serve system, the single compressive element dual check valve pump and the three element linear peristaltic pump are uniquely designed to be incapable of pumping gas at a significant discharge pressure. This is true because each of the two pump species is designed so that the pump lumen cannot be completely compressed or collapsed with pump displacement actuation. Because this is true, users of both the kitchen and self serve systems are uniquely protected from the expensive-like depressurization of gas embolisms which are frequently encountered within BIB packaged condiment products. These eruptions and rapid expansions of compressed gas pockets to atmosphere at the point of dispense are common and known problems with condiment dispenser systems utilizing other types of positive displacement pumps, particularly gas operated dual diaphragm pumps and gas operated piston type pumps.

While the best modes of this invention known to applicant at this time has been shown in the accompanying drawings and described in the accompanying text, along with variations of the illustrated best modes, it should be understood that applicant does not intend to be limited to the particular details illustrated in the accompanying drawings and described above. Thus, it is the desire of the inventors of the present invention that it be clearly understood that the embodiments of the invention, while preferred, can be readily changed and altered by one skilled in the art and that these embodiments are not to be limiting or constraining on the form or benefits of the invention.

What is claimed is:

1. A condiment dispensing apparatus for dispensing condiments from a condiment container, the condiments dispensing apparatus comprising:

support means (106 or 170) for supporting a condiment container (108 or 172);

a remote point of dispensing fixture (110, 158, 160, or 190);

pumping means (10 or 83) for pumping the condiment from the condiment container to the dispensing fixture, the pumping means including a high durometer compressible elastomeric liquid flow tube (14), an infeed valve assembly (12 or 84), an outfeed valve assembly (16 or 88), a discrete extensible and retractable displacement actuating assembly (18 or 84) including a movable actuator anvil (26) having a round surface which engages the flow tube (14) at all times, a spaced apart top anvil (28 or 90) mounted in a location directly opposite from the actuator anvil (26), the top anvil (28) having a round surface in engagement with the flow tube at all times, the flow tube being held between the movable actuating anvil and the top anvil in a slightly compressed state when the actuating assembly is retracted; and control means for controlling the operation of the pumping means, the control means including a start switch (64, 150, 152, or 192) located adjacent the dispensing fixture, the control means when started sequentially extending and retracting the displacement actuating assembly to cause flow within the flow tube (14) from a location adjacent the infeed valve assembly (12) to a location adjacent the outfeed valve assembly (16) to cause flow of condiment from the condiment container (108 or 172) to the dispensing fixture.

2. The condiment dispensing apparatus as set forth in claim 1 wherein the control means further includes means (36 or 186) to vary the stroke of the displacement actuating assembly (18 or 84) so that either partial compression of the flow tube is achieved during normal operation, or so that full compression of the flow tube is achieved during priming.

3. The condiment dispensing apparatus as set forth in claim 2 wherein the means to vary the stroke further includes means to create a priming mode wherein the stroke of the displacement actuating assembly is altered after a certain number of uninterrupted pump cycles to achieve full compression of the flow tube in order to maximize pump suction priming performances.

4. The condiment dispensing apparatus as set forth in claim 1 wherein the control means is electronic, and wherein the control means includes means to adjust time of movement of the displacement actuator assembly so that compressive displacement of the movable actuator assembly is achieved to allow direct electronic control over the displaced volume per pump cycle.

5. The condiment dispensing apparatus as set forth in claim 1 wherein the condiment is a condiment supply bag in a box (108), which bag has a spout (120) to which the pumping means is interconnected via a tube (112), and wherein the support means is a support frame (106) having a slanted upper surface (106.11–.15) to assist in the complete emptying of the supply bag.

6. The condiments dispensing apparatus as set forth in claim 5 wherein the slanted upper surface of the support frame is elevated for the purpose of accessibility to the spout.

7. The condiment dispensing apparatus as set forth in claim 5 for use with a cabinet (102, 104) having a compartment therein, further characterized by the support frame being mounted within the compartment with the slanted surface facing the front of the compartment so that installation and removed of the bag in a box is eased.

8. The condiment dispensing apparatus as set forth in claim 7 wherein the support frame is equipped with rear inboard mounted wheels (107) and front bottom mounted slide strips (107A) in order to allow easy partial withdrawal or insertion of the support frame out of or into the compartment of the cabinet.

9. The condiment dispensing apparatus as set forth in claim 1 wherein the support means is a support frame, the pump means being mounted flexible on the support frame by rubber or rubber-like straps.

10. The condiment dispensing apparatus as set forth in claim 1 wherein a positive shut-off valve (79 or 198) is disposed between the pumping means and the remote point of dispense for effecting cut-off of condiment flow to the point of dispense.

11. The condiment dispensing apparatus as set forth in claim 10 wherein the control means includes an electronic controller, and wherein the positive shut-off valve is controlled by the electronic controller.

12. The condiment dispensing apparatus as set forth in claim 1 wherein the pumping means is interconnected with the dispensing fixture by a flexible tube (114, 188), and wherein a positive shut-off valve (79, 198) is disposed between the pumping means and the remote point of dispense, which valve bears upon the flexible tube for effecting cut-off of condiment flow to the point of dispense.

13. The condiment dispensing apparatus as set forth in claim 1 wherein the apparatus may be connected to a source of warm or hot water for the purpose of cleaning, and which apparatus may be cleaned of condiments with no or little lipids by pumping less than three quarts (or three liters) of warm or hot water.

14. The condiment dispensing apparatus as set forth in claim 1 wherein two or more remote point of dispensing fixtures (158, 160) are provided, wherein there is a separate shut-off valve (154, 156) associated with each dispensing fixture, wherein the control means including an start switch (150, 152) located adjacent each dispensing fixture, wherein the control means including an start switch (150, 152) located adjacent each dispensing fixture, and wherein each start switch locks out the other start switches when operation of the pumping means is initiated to allow a single pumping means to service more than one dispensing fixture with the selected dispensing fixture receiving the complete flow or does from the pumping means.

15. The condiment dispensing apparatus as set forth in claim 14 wherein when a second start switch is closed during operation of the pumping means initiated by the closing of a first start switch, the second start switch must be opened after the first start switch initiated pumping has been completed in order for the second start switch to enter a start signal into the control means.

16. The condiment dispensing apparatus as set forth in claim 14 in which only one of the separate shut-off valves can be opened at any given time to assure that a correct dose is always delivered.

17. The condiment dispensing apparatus as set forth in claim 1 wherein two or more remote point of dispensing fixtures (158, 160) are provided, each fixture having an LED (16, 164) associated with it to indicate when the pumping means is in operation.

18. The condiment dispensing apparatus as set forth in claim 1 wherein the control means includes an electronic controller.

19. The condiment dispensing apparatus as set forth in claim 18 wherein a remote information port 166 is provided which may be interconnected to a remote information module so that information from the electronic controller may be assessed at a remote location.

20. The condiment dispensing apparatus as set forth in claim 19 wherein the electronic controller is provided with a remote information port (166), such port providing a steady state DC signal to the remote information module whenever the condiment dispenser is in an operable condition, and wherein loss of the DC signal to the remote information module for a period of more than two seconds signifies loss of operable condition of the dispenser.

21. The condiment dispensing apparatus as set forth in claim 19 wherein the electronic controller senses a lack of condiment at the dispenser, the electronic controller being provided with a remote information port (166), such port providing a DC pulsating signal at a frequency of approximately one Hertz when there is a lack of condiment at the dispenser, and wherein the condition may be annunciated by a rapidly pulsating status LED at the dispensing fixture, or elsewhere.

22. The condiment dispensing apparatus as set forth in claim 19 wherein the electronic controller is provided with a remote information port (166), the remote information port providing a 10 mS pulse with each pump cycle, thus allowing the remote information module to measure condiment consumption at the dispense and to allow prediction of an empty condiment supply condition.

23. The method for dislodging the vehicle as set forth in claim 22 wherein the longitudinal movement is in a forward direction.

24. The method for dislodging the vehicle as set forth in claim 22 wherein the longitudinal movement is in a rearward direction.

25. The condiment dispensing apparatus as set forth in claim 18 wherein the infeed valve assembly and the outfeed valve assembly are discrete check valve assemblies (12 and 16, respectively), wherein a positive shut-off valve (79, 154, 156) is located near the dispensing fixture, the positive shut-off valve being controlled by the electronic controller, and wherein operation of the electronic controller is initiated by a flow switch (64, 150, 152), so that the condiment dispensing apparatus is capable of pumping viscous condiments 40 feet from the pump without significant latency of flow from moment of flow switch actuation.

26. The condiment dispensing apparatus as set forth in claim 18 wherein the infeed valve assembly and the outfeed valve assembly are discrete infeed and outfeed extensible and retractable actuating assemblies, wherein a positive shut-off valve is located near the dispensing fixture, which valve is controlled by the electronic controller, and wherein operation of the electronic controller is initiated by a flow switch, so that the condiment dispensing apparatus is capable of pumping smooth condiments 100 feet from the pump without significant delay of flow from moment of flow switch actuation, the positive shut-off valve shutting off flow at the end of pumping thus assuring that with the next dispensing cycle the pump is not required to pump the outfeed structure up to some pressure where flow ensues, flow thus occurring on a nearly instantaneous basis upon opening of the shut-off valve by the pump electronic controller.

27. The condiment dispensing apparatus as set forth in claim 18 wherein the infeed valve assembly (26) and the outfeed valve assembly (38) are discrete infeed and outfeed extensible and retractable actuating assemblies, the electronic controller sequentially extending and retracting the actuating assemblies (26, 36, 38) to cause flow of a one third ounce dose of ketchup to be delivered at a distance of 25 feet from the pumping means in less than 500 milliseconds.

28. The condiment dispensing apparatus as set forth in claim 1 wherein the condiment dispensing apparatus has more than one pumping means (83), and wherein a condiment container (172)is provided for each pumping means.

29. The condiment dispensing apparatus as set forth in claim 28 wherein each condiment container is a condiment supply bag in a box (172), which bag has a spout (176), each spout being connected to an associated pumping means (83).

30. The condiment dispensing apparatus as set forth in claim 29 wherein the support means (170) is capable of supporting all the condiment supply bags in boxes, each condiment bag in box being mounted on its narrow edge with its spout projecting through a hole (178) in the support means thus allowing a minimal and compact dimension for the condiment stand and allowing manipulation of the condiment as a boxed unit.

31. The condiment dispensing apparatus as set forth in claim 30 wherein each condiment supply bag in a box is mounted directly above an associated pumping means (83) with the pumping means being mounted vertically with the infeed side at the top and the outfeed side at the bottom such that direct flood feed of the pump is established thus speeding pump priming and enhancing pump flow rates.

32. The condiment dispensing apparatus as set forth in claim 28 wherein the remote point of dispensing fixture is a dispensing wand which is capable of simultaneously dispensing with the actuation of a single switch of two or more condiments, thus reducing the time required to deposit desired condiments.

33. The condiment dispensing apparatus as set forth in claim 1 wherein the support means is a frame (170) capable of supporting two or more condiment containers, and wherein the frame is also capable of supporting two or more pumping means, one for each condiment container, the frame being so designed that varying numbers of condiment containers and pumping means can be mounted thereon in a modular manner.

34. The condiment dispensing apparatus as set forth in claim 1 wherein the pump means is mounted on a pump frame consisting of two parts, a check valve mounting plate (20) and an upper anvil mounting plate (22), the check valve mounting plate having platforms (20.3) disposed above the plane of a flat section (20.1), and the upper anvil mounting plate being secured to the flat section of the check valve mounting plate.

35. The condiment dispensing apparatus as set forth in claim 34 wherein the infeed and outfeed valve assemblies are check valve assemblies, which valve assemblies are mounted on the check valve mount plate.

36. The condiment dispensing apparatus as set forth in claim 35 wherein each of the check valve assemblies includes a valve body, infeed and outfeed barbs, and a check valve cartridge and ball mounted within the valve body, the valve body being secured to the platforms (20.3) by cable tie fasteners.

37. The condiment dispensing apparatus as set forth in claim 34 wherein the extensible and retractable displacement actuating assembly includes a cylinder (30) having a threaded nosepiece, and wherein the check valve mounting plate (20) and an upper anvil mounting plate (22) are each provided with a central aperture through which the threaded nose piece projects, the cylinder (30), and mounting plate (20 and 22) being secured together by a nut (34).

38. The condiment dispensing apparatus as set forth in claim 1 wherein the pumping means includes a pump housing, wherein the infeed and outfeed valve assemblies are check valve assemblies which are mounted on the pump housing, the infeed and outlet valve assemblies having barbs in axial alignment with each other, and wherein the high durometer compressible elastomeric liquid flow tube (12) is mounted on adjacent barbs of the inlet and outlet valve assemblies in such a manner that the tube is concentric with the burbs.

39. The condiment dispensing apparatus as set forth in claim 1 wherein the lumen of the flow tube is not completely reduced to zero volume during displacement compressing when normally dispensing condiment whereby gas embolisms do not erupt or explode when condiment is discharged at the point of dispense.

40. The condiment dispensing apparatus as set forth in claim 1 wherein the lower compression anvil (26) is a cylinder, wherein the top anvil (28) is a separate and removable cylinder, the diameter of the separate and removable cylinder being substantially the same as the diameter of the cylinder utilized as the lower compression anvil.

41. The condiment dispensing apparatus as set forth in claim 40 wherein an upper anvil mounting plate (22) is provided for mounting the top anvil (28), the upper anvil mounting plate having spaced apart sidewalls which are suitably apertured for the reception of the top anvil, and wherein the top anvil is provided with a groove at either end, which grooves are captured by the sidewalls to retain the top anvil in place.

42. The condiment dispensing apparatus as set forth in claim 1 wherein the discrete extensible and retractable displacement actuator assembly includes a pneumatic cylinder assembly having a cylinder rod upon which the displacement anvil is mounted by a spring pin which is pressed into the anvil and into a matching hole in the end of the cylinder rod.

43. The condiment dispensing apparatus as set forth in claim 1 wherein the extensible and retractable displacement actuating assembly is a pneumatic cylinder assembly, and wherein the air into and out of the cylinder assembly is controlled by a pneumatic solenoid valve (68).

44. The condiment dispensing apparatus as set forth in claim 1 wherein the extensible and retractable displacement actuating assembly is a pneumatic cylinder assembly, and wherein means are provided to independently adjust the retraction time of the pneumatic cylinder assembly beyond a necessary minimum time to allow for increased liquid priming time thus increasing the range of liquid viscosities over which the pump can function.

45. The condiment dispensing apparatus as set forth in claim 1 wherein the control means includes an electronic controller (186), the electronic controller including a selector switch (62) to allow selection between an on demand mode of operation and a timed dose mode of operation.

46. The condiment dispensing apparatus as set forth in claim 45 wherein a momentary start switch (64) is mounted adjacent the dispensing fixture to initiate operation of the pumping means, the momentary start switch being interconnected with the electronic controller, and when the selector switch is set to the demand mode, closing of the momentary start switch will initiate pumping, which pumping will continue until the momentary start switch is released.

47. The condiment dispensing apparatus as set forth in claim 45 wherein a momentary start switch (64) is mounted adjacent the dispensing fixture to initiate operation of the pumping means, the momentary start switch being interconnected with the electronic controller, and when the selector switch is set to the timed dose mode, closing of the momentary start switch will initiate pumping, which pumping will continue until the desired dose is delivered, regardless of whether the start switch is maintained actuated or is released.

48. The condiment dispensing apparatus as set forth in claim 47 wherein the momentary start switch must be released after the end of the dose before another start input can be accepted by the electronic controller.

49. The condiment dispensing apparatus as set forth in claim 1 wherein the remote point of dispensing fixture includes a rigid support (190) through which a flexible tube (188) extends.

* * * * *

UNITED STATES PATENT AND TRADEMARK OFFICE
CERTIFICATE OF CORRECTION

PATENT NO.    : 6,189,736 B1
DATED         : February 20, 2001
INVENTOR(S)   : Iver J. Phallen et al It is certified that error appears in the above-identified patent and that said Letters Patent is hereby corrected as shown below:

Claim 1,
Lines 1-2, "condiments" should be -- condiment --;
Line 2, "condiments" should be -- condiment --;

Claim 5,
Line 2, after :condiment" (first occurrence) insert -- container --;

Claim 7,
Line 6, change "removed" to -- removal --;

Claim 9,
Line 3, change "flexible" to flexibly --;

Claim 13,
Line 3, change "purpose" to -- purposes --;

Claim 14,
Lines 5 and 6, delete "wherein the control means including an start switch (150, 152) located adjacent each dispensing fixture'";

Claim 19,
Line 5, change "assessed" to -- accessed --;

Cancel claims 23 and 24 and insert the following claims:
-- 23. The condiment dispensing apparatus as set forth in claim 18 wherein the infeed valve assembly and the outfeed valve assembly are discrete infeed and outfeed extensible and retractable actuating assemblies (86 and 88, respectively), and wherein the electronic controller can be operated in such a manner as to provide adjustable back pumping of the pumping means to provide rapid cut-off of condiment flow substantially free of ooze and drip at a distance of up to 20 feet from the outfeed valve assembly.

UNITED STATES PATENT AND TRADEMARK OFFICE
CERTIFICATE OF CORRECTION

PATENT NO. : 6,189,736 B1
DATED : February 20, 2001
INVENTOR(S) : Iver J. Phallen et al It is certified that error appears in the above-identified patent and that said Letters Patent is hereby corrected as shown below:

-- 24. The condiment dispensing apparatus as set forth in claim 18 wherein the infeed valve assembly and the outfeed valve assembly are discrete infeed and outfeed extensible and retractable actuating assemblies (86 and 88, respectively), wherein a positive shut-off valve (79, 198) is located near the dispensing fixture, which valve is controlled by the electronic controller, and wherein operation of the electronic controller is initiated by a flow switch (64,192), so that the condiment dispensing apparatus is capable of pumping viscous particulated condiments 40 feet from the pump without significant latency of flow from moment of flow switch actuation. --

Claim 37,
Line 7, change "plate" to -- plates --;

Claim 38,
Line 10, change "burbs" to -- barbs --; and

Column 39,
Line 3, change "compressing" to -- compression --.

Signed and Sealed this

Twenty-fifth Day of December, 2001

*Attest:*

*Attesting Officer*

JAMES E. ROGAN
*Director of the United States Patent and Trademark Office*